(12) United States Patent
Jang

(10) Patent No.: US 7,289,210 B2
(45) Date of Patent: Oct. 30, 2007

(54) CIRCULARLY POLARIZED LIGHT METHOD AND DEVICE FOR DETERMINING WALL THICKNESS AND ORIENTATIONS OF FIBRILS OF CELLULOSIC FIBRES

(75) Inventor: Ho Fan Jang, Vancouver (CA)

(73) Assignee: FPInnovations, Pointe-Claire, Quebec (CA)

( * ) Notice: Subject to any disclaimer, the term of this patent is extended or adjusted under 35 U.S.C. 154(b) by 278 days.

(21) Appl. No.: 10/996,423

(22) Filed: Nov. 26, 2004

(65) Prior Publication Data
US 2005/0122514 A1 Jun. 9, 2005

Related U.S. Application Data

(60) Provisional application No. 60/526,280, filed on Dec. 3, 2003.

(51) Int. Cl.
G01J 4/00 (2006.01)

(52) U.S. Cl. .................................................. 356/364

(58) Field of Classification Search ................ 356/364, 356/246, 365; 928/938
See application file for complete search history.

(56) References Cited

U.S. PATENT DOCUMENTS 4,171,916 A 10/1979 Simms et al.

(Continued)

FOREIGN PATENT DOCUMENTS

CA 1153578 9/1983

(Continued)

OTHER PUBLICATIONS

"Photopolarimetric Measurement of Single, Intact Pulp Fibers by Mueller Matrix Imaging Polarimetry" by Chun Ye; Apr. 1, 1999 / vol. 38, No. 10 / Applied Optics, pp. 1975-1985.

(Continued)

Primary Examiner—Tarifur Chowdhury
Assistant Examiner—Jonathon D Cook
(74) Attorney, Agent, or Firm—Ogilvy Renault LLP

(57) ABSTRACT

This invention provides a novel, rapid method and device for determining the relative phase retardation of different layers of a multi-layered specimen, which is related to the thicknesses of its layers and walls, and the orientations of its optical axes. An intact wood pulp fibre is a typical multi-layered birefringent specimen. This new method is based on the change of polarization of polarized light that passes through a specimen composed of birefringent layers with different optical axis orientations, such as directions of cellulosic microfibrils oriented differently in various layers of wood fibres. In particular, a novel solution is found to relate the emerging light intensity from an intact wood fibre to the incident light intensity, the wavelength of the light, and the relative phase retardations of various layers and orientations of their cellulosic microfibrils, such as fibril angle, in a circularly polarized light system. This new method evaluates the transmitted light intensities of multiple predetermined wavelengths simultaneously to determine the optical and physical properties of a multi-layered specimen being measured. A device for determining the relative phase retardation (retardance) of fibre walls and the fibril angle of intact wood fibres in accordance with the presented invention comprises a light source with well defined multi-wavelengths, an achromatic circularly polarized light system, appropriate imaging optics, a multi-channel camera such as a digital color camera that has two or more wavelength (color) detection channels, and an image processing and data analysis system. The measurements take advantage of the birefringence of cellulosic microfibrils, and thus require neither sample preparation nor high resolution optics. Specimen alignment is not required as specimens such as wood fibres are evaluated under circularly polarized light. Compared with other methods, this invention is more rapid, accurate, and robust. This method can be automated, and implemented in a fibre flow-through system, thus allowing a rapid assessment of wood pulp fibre properties (on-line in real time).

15 Claims, 15 Drawing Sheets

U.S. PATENT DOCUMENTS

| | | | |
|---|---|---|---|
| 4,654,529 A | 3/1987 | Boulay et al. | |
| 4,955,720 A | 9/1990 | Blecha et al. | |
| 5,500,735 A * | 3/1996 | Bentley et al. | 356/364 |
| 5,521,705 A * | 5/1996 | Oldenbourg et al. | 356/368 |
| 5,606,418 A * | 2/1997 | Borden et al. | 356/364 |
| 5,917,598 A | 6/1999 | Mason | |
| 6,567,213 B2 | 5/2003 | Rosencwaig et al. | |
| 7,002,685 B2 * | 2/2006 | Wang | 356/364 |
| 7,061,614 B2 * | 6/2006 | Wang et al. | 356/369 |
| 2003/0106163 A1 * | 6/2003 | Neogi et al. | 8/116.1 |
| 2003/0179375 A1 | 9/2003 | Wang | |
| 2004/0125373 A1 | 7/2004 | Oldenbourg et al. | |

FOREIGN PATENT DOCUMENTS

| | | |
|---|---|---|
| CA | 2261469 | 8/1999 |
| EP | 1435517 | 7/2004 |
| JP | 1996201276 A | 8/1996 |
| WO | WO 96/10168 | 4/1996 |

OTHER PUBLICATIONS

"Estimation of Lignin Content in Single, Intact Pulp Fibers by UV Photometry and VIS Mueller Matrix Polarimetry" by Chun Ye, Nordic Pulp and Paper Research Journal vol. 16, No. 2/2001, pp. 143-148.

* cited by examiner

Wet, λ = 450 nm

Dry, λ = 450 nm

Wet, λ = 530 nm

Dry, λ = 530 nm

Wet, λ = 640 nm

Dry, λ = 640 nm

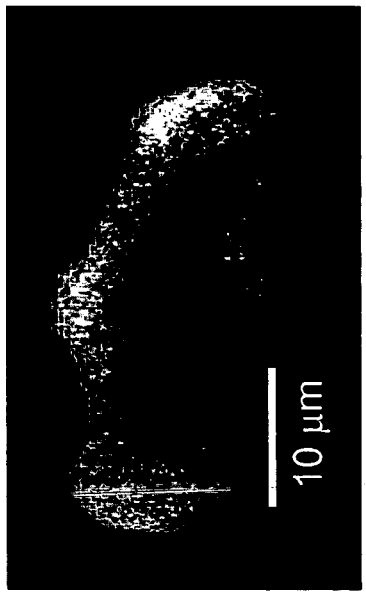
CLSM image Fig. 9b
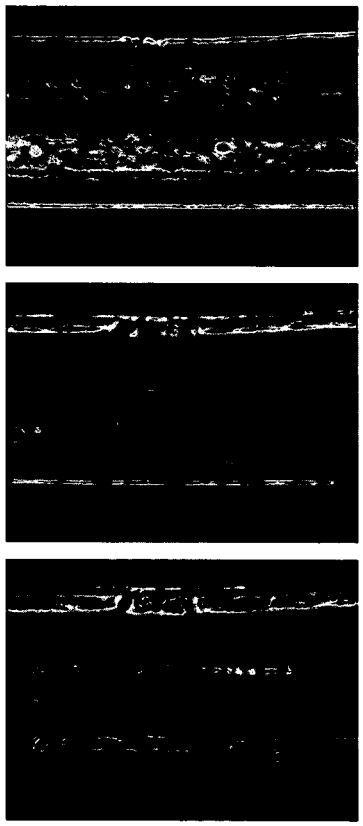
CPLM images Fig. 9a
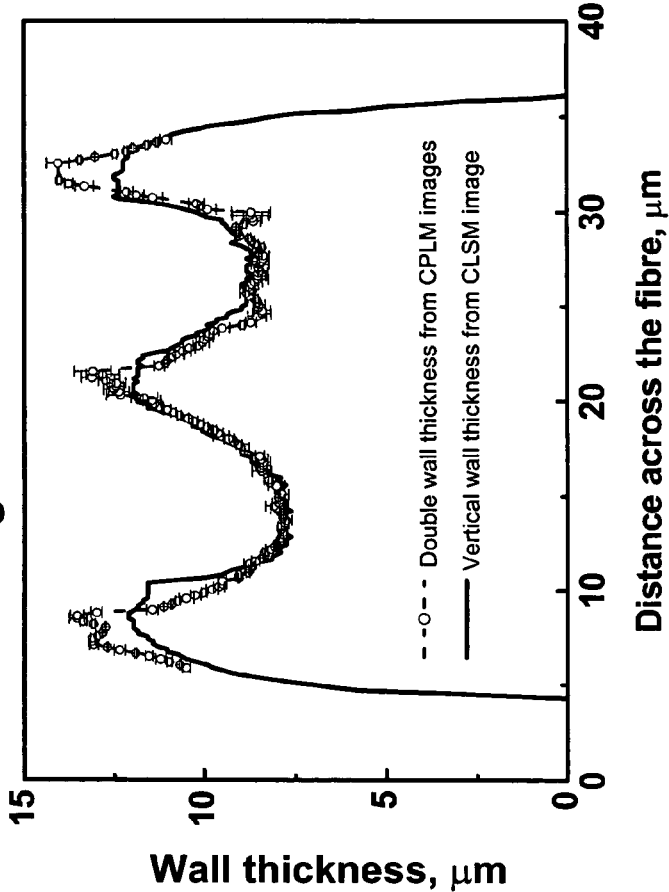
Fig. 9c

CIRCULARLY POLARIZED LIGHT METHOD AND DEVICE FOR DETERMINING WALL THICKNESS AND ORIENTATIONS OF FIBRILS OF CELLULOSIC FIBRES

CROSS-REFERENCE TO RELATED APPLICATION

This application claims priority under 35 U.S.C. 119(e) from U.S. Provisional Application Ser. No. 60/526,280, filed Dec. 3, 2003.

BACKGROUND OF THE INVENTION i) Field of the Invention

The present invention relates to polarized light, optical and all related physical properties of a birefringent specimen, and in particular, to a polarized light method and device for determining the relative phase retardations, and the orientations of the optical axes of different layers in a multi-layered birefringent specimen, preferably, the relative phase retardation, which is related to the wall thickness, and the fibril angle of intact wood pulp fibres.

ii) Description of the Prior Art

A wood fibre, an example of a cellulosic fibre, is a biological material consisting of four principal layers: the primary wall $P_1$, and the three secondary wall layers $S_1$, $S_2$ and $S_3$ as shown in FIG. 1(a) [1]. All three secondary layers are composed of long crystalline cellulosic microfibrils, embedded in an amorphous matrix of hemicelluloses and lignin. The outer $S_1$ and the inner $S_3$ layers are very thin and their microfibrils are wound almost transversely to the fibre axis. The middle $S_2$ layer, comprising 80-90% of the fibre-wall material, has cellulosic microfibrils wound in a helix at an angle, termed the fibril angle ($\theta$), to the longitudinal fibre axis. The crystalline microfibrils are aligned in these layers, and are birefringent, making wood fibres birefringent. The magnitude of the birefringence depends on the thickness of the layers $S_1$, $S_2$ and $S_3$, the orientations of their microfibrils, and the birefringence of each layer.

The fibre wall thickness and the fibril angle in the dominant $S_2$ layer control the physical and mechanical properties of wood pulp fibres, and therefore strongly influence the response of pulps to papermaking treatments and the end-use properties of paper and board products. For instance, fibre wall thickness affects virtually all physical properties of paper including structural, strength and optical characteristics [2, 3]. Fibril angle, on the other hand, controls swelling/shrinkage properties [4], stress-strain behaviour [5] and dimensional stability of paper [6]. It has been shown that the $S_2$ fibril angle strongly affects the collapsibility of fibres. The knowledge of important fibre properties such as fibre wall thickness and fibril angle is, therefore, critical for identifying and selecting resources that are optimal for a given end use. Unfortunately, due to the microscopic size of fibres, both fibre wall thickness and fibril angle are difficult to measure. Moreover, all fibre properties are heterogeneous in nature. The information on the distributions of fibre properties is considered to be very important in controlling pulp quality as it maps the extent of heterogeneity in a pulp, and allows identification of the amount of fibres with certain properties [2]. Thus, it is critically important to devise rapid techniques for quantifying individual fibre properties such as wall thickness and fibril angle in pulps.

Recently, a new instrument, the Kajaani FibreLab fibre analyzer, has provided measurements for fibre width and cell wall thickness of fibres flowing through a capillary tube [P1]. The principle of this instrument is based on the projected two-dimensional image of a fibre. This measurement technique is quite adequate for fibre width, which has dimensions in the range of tens of microns. However, this direct imaging technique faces many difficulties for accurate measurements of fibre wall thickness, which varies greatly from less than one μm to several μm. Recent investigation has shown that fibre wall thickness measurements from the Kajaani FibreLab are grossly incorrect [7].

The most reliable current techniques for determining wall thicknesses of wood pulp fibres are based on the fibre cross-sectional images, which can be generated by a Scanning Electron Microscope (SEM) on prepared fibre sections [8], or generated non-destructively by using the optical sectioning ability of confocal laser scanning microscopy (CLSM) [9]. When combined with image analysis, these techniques are capable of accurately measuring individual fibre transverse dimensions, such as wall thickness [4]. Although this technique provides valuable information on fibre transverse dimensions and is a good research tool, it is too slow for most practical industrial purposes. Thus, a rapid and accurate technique for measuring the wall thickness of individual wood pulp fibres is still lacking.

As mentioned earlier, fibril angle is another important fibre property. Several methods have been developed to measure fibril angle in wood pulp fibres: polarized-light microscopy [10], direct observation [11], micro-Raman spectroscopy [12], orientation of the elongated pit apertures [13], and most recently polarization confocal microscopy [13]. Although these techniques can provide measurements on fibril angles, they are also very slow.

Techniques based on polarized-light microscopy have been used for many years for measuring fibril angle in wood pulp fibres. These techniques make use of the natural birefringence of cellulose fibrils, and unequal retardations/refractive indexes in the directions parallel and perpendicular to the micofibrils. The direction of the fibrils in a single layer of the fibre wall can be readily obtained by examining the wall between crossed polars. However, this procedure requires a single wall; it cannot be used for intact fibres, as the opposite wall of the helically wound fibre interferes. This difficulty has been overcome, for example, by observing a single wall through a bordered pit, or by examining a single wall obtained by longitudinal microtome sectioning. A method for pulp fibres was developed by Page [10] in which a single wall is observed by reflecting light from mercury inserted into the fibre lumen. The fibril angle of the $S_2$ layer is determined from the extinction positions for the (single) wall observed between crossed polars. Though simple in principle, this technique is tedious and hazardous, and is subject to errors from the $S_1$ and $S_3$ layers [14].

Most recently, developments based on transmission polarimetry techniques by Ye et al. [15, 16, 18] and Ye [P2, 17] claimed to be able to determine non-destructively the phase retardation $\Delta$, and the fibril angle $\theta$ of the $S_2$ layer on intact wood pulp fibres. There are many limitations on their methods. One major shortcoming of the above methods is that the influence of the $S_1$ and $S_3$ layers are neglected. In fact, the effects of the transversely wound $S_1$ and $S_3$ layers on the birefringence of intact softwood fibres are significant, particularly for thin-walled fibres, as shown by Page et al. [19]. It has also been shown by El-Hosseiny et al. [14] that the birefringent $S_1$ and $S_3$ layers, although thin, cannot be ignored in fibril angle measurements based on the polarized light method. Therefore, neglecting the effects of the birefringent $S_1$ and $S_3$ layers creates serious errors for measurements of both wall thickness and fibril angle. Moreover, as discussed in Ye's paper [17], the method based on a polarizer-sample-analyzer arrangement and the mathematical analysis by Ye at al. [15, 16] and Ye [P2] has many limitations. For example, the fibre sample in Ye's method [P2] has to be aligned to a certain orientation relative to the polarizer. Moreover, at least four intensity measurements at various analyzer orientations with the polarizer orientation fixed are required for calculating $\Delta$ and $\theta$. Because the derived expressions for $\Delta$ and $\theta$ are in quadratic form, the results for $\Delta$ and $\theta$ are ambiguous. To avoid the ambiguity, the measurement has to be carried out for at least two wavelengths, and the user needs to distinguish the physically relevant results from two groups of intermediate ones. This method is not reliable, and can lead to misinterpretation of the data. Because of all these limitations, it will not work in an automatic, and definitely not in an on-line system. A new improved technique based on Muller matrix polarimetry was proposed by Ye [17]. Ye claimed that the newer method permits quantitative and non-destructive determinations of $\Delta$ and $\theta$ from measurements at one wavelength, and one advantage of his newer method is the feasibility of simultaneous measurements of several fibres at different orientations as the fibre orientation can also be obtained from the measurements. However, the method still needs many measurements obtained with the analyzer, polarizer and/or the retarders oriented at different angles, and it takes a very long time to make measurements on stationary fibres. Both of these techniques are very time consuming, and unsuitable for on-line type instruments.

The use of polarizing filters to generate a visual contrast for imaging birefringent fibres is not new. Many commercial fibre length analyser such as the Kajaani fibre length analyser (Kajaani Electronics Ltd, Finland), and the Fibre Quality Analyser (OpTest, Canada) [P3] have adopted such optical techniques for wood fibre length or/and shape measurements; individual fibres are imaged while they are flowing through a capillary tube or a flow-through cell. Although these instruments can measure fibre length rapidly, they cannot provide measurements on either fibre wall thickness or fibril angle. Therefore, there is still a need to develop a rapid and accurate technique for measuring fibre wall thickness and fibril angle of individual fibres in a way that is similar to the fibre length measurements.

The present invention aims at developing a new, rapid technique for measuring fibre wall thickness and fibril angle using a non-destructive optical technique that is based on circularly polarized light microscopy. The new invention provides a means to determine distributions of fibre properties because it is based on single fibre measurements. Properties of fibres are determined by analyzing the intensities of multi-wavelength light emerging from the system. This new invention can be automated, and implemented in a fibre flow-through system, thus allowing a rapid assessment of wood fibre properties (on-line in real time).

SUMMARY OF THE INVENTION

It is an object of this invention to provide a method for determining optical and physical properties of a multi-layered birefringent specimen, for example a wood pulp fibre.

It is another object of this invention to provide a new method and device for measuring the phase retardations of multi-layered birefringent specimens at different wavelengths, and the orientations of their optical axes, especially in wood pulp fibres.

It is still another object of this invention to provide a method that permits non-destructive, rapid, simple and accurate measurements of the phase retardations of multi-layered birefringent specimens at different wavelengths simultaneously, and the orientations of their optical axes, especially in wood pulp fibres.

In one aspect of the invention, there is provided a method for determining at least one parameter selected from relative phase retardations and orientations of the optical axes of a multi-layered birefringent specimen comprising the steps of: producing a circularly polarized light beam having a plurality of wavelengths, wherein the plurality is at least the same number as the number of parameters to be determined in the multi-layered specimen under evaluation; impinging the circularly polarized light beam on the specimen to be evaluated; recording and measuring the light intensities of the wavelengths emergent from the specimen; and determining the at least one parameter from the light intensities of the emergent wavelengths and fitting the data with an equation that describes the specimen.

In another aspect of the invention, there is provided a method for determining the relative phase retardation, related to wall thickness, and fibril angle of an intact wood fibre having a wall comprised of three layers $S_1$, $S_2$ and $S_3$: the two outside layers $S_1$ and $S_3$ having microfibrils oriented transversely with respect to the fibre longitudinal axis, and the middle dominant layer $S_2$ having microfibrils wound in a helix at fibril angle comprising the steps of: producing a circularly polarized light system beam, at at least two wavelengths; impinging the circularly polarized light beam on a wood fibre to be measured; recording and measuring the light intensities of the wavelengths emergent from the wood fibre; and determining the relative phase retardations and hence the wall thickness, and the $S_2$ fibril angle of the wood fibre from the light intensities of the wavelengths emergent from the wood fibre, and fitting the data with an equation that describes the wood fibre.

In still another aspect of the invention, there is provided an apparatus for determining relative phase retardations, or orientations of the optical axes of a specimen comprising a light source effective to provide light in multiple wavelengths, a circularly polarized light system to generate a circularly polarized light beam from the light from said light source, means to dispose a specimen within said system, in the path of the generated circularly polarized light beam, means for determining the light intensities of light emergent from the specimen, and processing means to determine the properties of the specimen from the emergent light intensities.

DETAILED DESCRIPTION OF THE INVENTION

The method of the invention may be carried out with the circularly polarized light in a dark field or a bright field.

The light source is typically of multiple predetermined and well-defined wavelengths, and the number of predetermined wavelengths is suitably at least the same as the number of parameters, to be determined.

The method may suitably be employed to determine the relative phase retardations, or the orientations of the optical axes of the specimen, or both.

The circularly polarized light system employed is suitably comprised of a polarizer and an analyzer; both the polarizer and the analyzer may be linear polarizers; and a pair of well-matched achromatic quarter-wave retarders with a working wavelength range covering all predetermined wavelengths of the light source. The optical axes of the retarders are oriented 90° to each other and 45° to the polarizer and the analyzer.

The apparatus suitably includes, for determining light intensities of light emergent from the specimen: a condenser and an objective lens for microscopic polarized light imaging; the image capturer which may suitably be a multi-wavelength detector or a camera, for example a multi-channel digital camera; an image processing and an image and data analysis system comprising an image processor for multiple images to determine the light intensities at individual, predetermined wavelengths, and an image analyzer, for example, having analyzer programs for analyzing multiple images and identifying the region of interest for data analysis.

The data analysis is suitably carried out with a non-linear fitting routine for determining the properties, especially the relative phase retardations and the orientations of the optical axes of the specimen, from the intensities of multi-wavelength data emergent from the circularly polarized light system with an equation describing the specimen being measured.

Suitably, the light source provides a number of predetermined wavelengths that are well separated, but are still within the acceptable working wavelength range of the achromatic quarter-wave retarders. The predetermined wavelengths may suitably range from 250 nm to 1000 nm.

The multi-layered birefringent specimen is suitably selected from cellulosic fibres consisting of wood and non-wood fibres, and wood and non-wood pulp fibres.

A particular advantage of the present invention is that it is not necessary to position or orient the specimen relative to the circular polarized light beam in which it is disposed. Similarly, it is not necessary to adjust, for example by rotation, the analyzer of the emergent light.

The specimen is thus in a non-restricted orientation in the beam.

Thus, in one embodiment, this invention provides a new polarized-light method as the solution for determining both the phase retardations of multi-layered birefringent specimens at different wavelengths and the orientations of their optical axes, especially the wall thickness and fibril angle of wood pulp fibres.

The number of individual wavelengths needed in the system depends on the number of unknown parameters in a specimen being measured.

A device for use in the method is comprised of: a) a predetermined multi-wavelength light source, b) a circularly polarized light microscopy system, c) a multi-channel imaging system for detecting the predetermined multi-wavelength light intensities, such as a color digital camera, and d) an image processing and data analysis system.

The circular polarization system suitably consists of a polarizer, an analyzer, and a pair of "well-matched" quarter-wave achromatic retarders in the wavelength region of the measurements. These components can be arranged to provide a circularly polarized light system with either dark- or bright-field (i.e. dark or bright background).

This invention relies mainly on the birefringent properties of specimens at different wavelengths, and the apparatus or measurement instruments, to provide and implement a method to measure the phase retardations of multi-layered birefringent specimens at different wavelengths, and the orientations of their optical axes simultaneously, especially wall thickness and fibril angle of wood pulp fibres.

Besides wood fibres, this measurement technique is suitable to characterize any other single- and multi-layered birefringent specimens such as non-wood fibres; e.g., cotton, ramie, kenaf and flax fibres, etc.

BRIEF DESCRIPTION OF THE DRAWINGS

FIGS. 9(a), (b) and (c) show (a) micrographs of a fibre segment in the CPLM system at wavelengths 450, 530 and 640 nm, (b) a confocal cross-sectional image generated from the fibre segment, and (c) double wall thickness determined by analyzing the CPLM micrographs, and the vertical wall thickness generated from CLSM image.

DETAILED DESCRIPTION OF THE INVENTION

Figure 1:
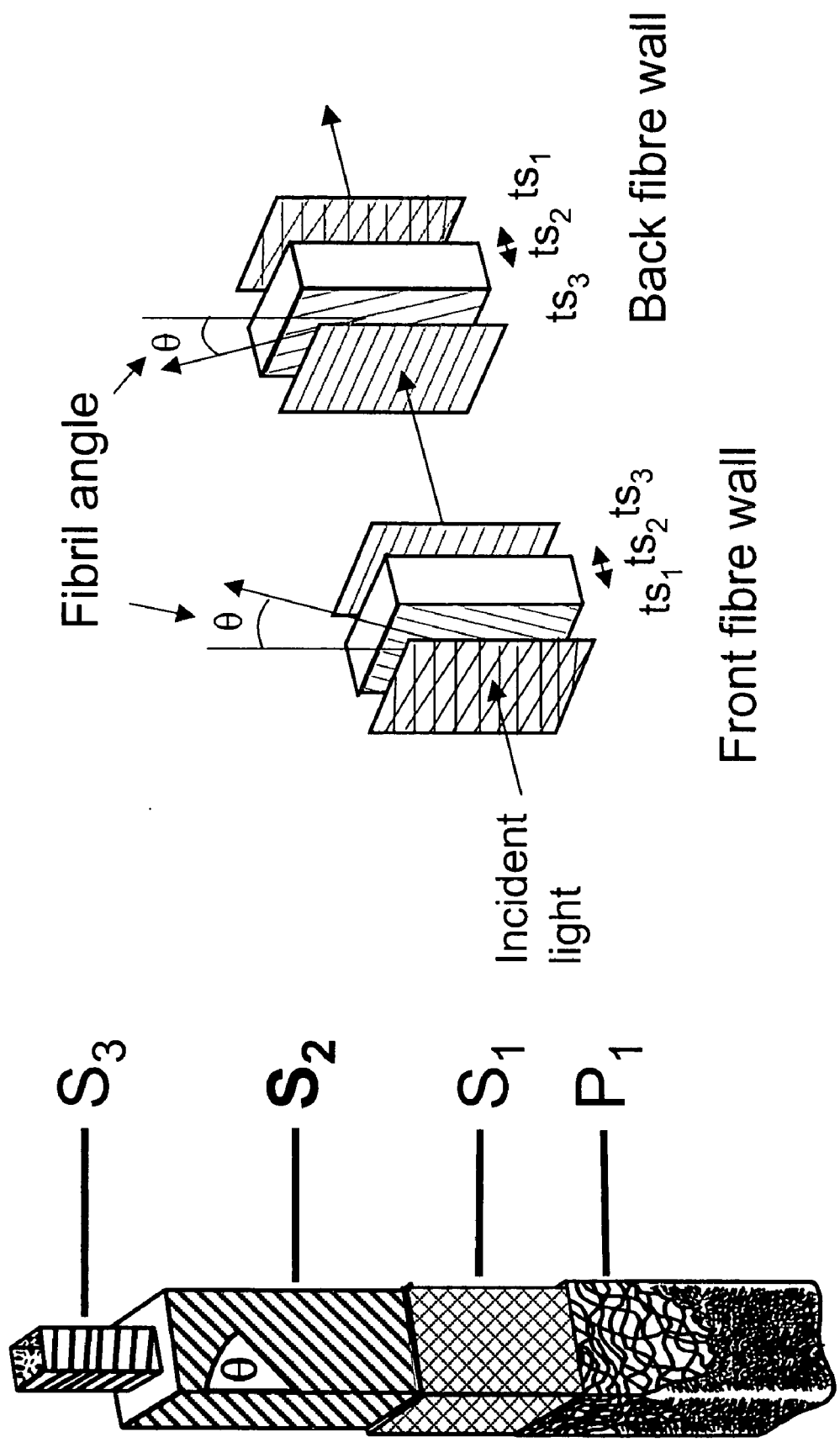
FIGS. 1(a) and (b) show (a) a schematic representation of layer structure of a single wood fibre, and illustrates (b) the model for describing an intact fibre used in this invention. Each fibre wall consists of three layers, $S_1$, $S_2$ and $S_3$ that are represented by three birefringent layers with different thicknesses $ts_1$, $ts_2$ and $ts_3$. The directions of the optical axes for $S_1$ and $S_3$ are approximately 90° with respect to the fibre axis, but this angle is θ for $S_2$ layers. The two opposite fibre walls are assumed to have identical wall thicknesses, but opposite θ (i.e., ±θ) in the $S_2$ layers.

The principle of the technique of the invention is based on measuring the change in polarization of light passing through a birefringent specimen, such as an intact wood pulp fibre. When the incident light has well defined polarization with multiple wavelengths, measuring the polarizations of the multi-wavelength emergent light provides a means to determine the thicknesses of multi-layered specimens and the orientations of their optical axes, such as wall thickness and fibril angle of wood pulp fibre. First is described the polarization transmission property of a multi-layered specimen, including wood pulp fibres; the change of polarization depends on the wavelength of the light and the birefringence of the cellulosic microfibrils, wall thickness and microfibril orientations of each layer in the specimen.

Optical Properties of Wood Pulp Fibres

The Jones matrix formalism is used to describe light propagating through a specimen under a polarized light system [20, 21]. If all optical axes of the material are positioned perpendicular to the direction of the propagation of the light beam, a 2×2 Jones matrix that describes the transmission property of the material, T, is $$T = \begin{pmatrix} a & b \\ c & d \end{pmatrix}, \quad (1)$$

where its elements $T_{ij}$–a, b, c, d are complex variables in general (for example, $a=a_1+ja_2$). For a specimen or optical system that has birefringence but no absorption, the Jones matrix T is unitary, whose elements $T_{ij}$ have the following properties: $a^2+b^2=1$, $a=d^*$, and $c^*=-b$ (the symbol asterisk "*" denotes a complex conjugate). For example, a is the complex conjugate of d, i.e., $a=a_1+ja_2=d_1-jd_2$.

For example, for a single layer birefringent specimen with its optical axis, such as the direction parallel to the cellulosic microfibrils, oriented at an angle θ from its vertical axis, the Jones matrix is:

$$T(\Delta, \theta) = R(-\theta)\begin{pmatrix} e^{j\Delta/2} & 0 \\ 0 & e^{-j\Delta/2} \end{pmatrix} R(\theta) \quad (2)$$

where $$R(\theta) = \begin{pmatrix} \cos\theta & \sin\theta \\ -\sin\theta & \cos\theta \end{pmatrix}, \quad (3)$$

is the rotation matrix, and $$\Delta = (\Delta_\| - \Delta_\perp) = \frac{2\pi t}{\lambda}(n_\| - n_\perp), \quad (4)$$

is the relative phase retardation; the components of the electric vector along the directions parallel and perpendicular to the optical axis are retarded by different amounts $\Delta_\|=2\pi t n_\|/\lambda$ and $\Delta_\perp=2\pi t n_\perp/\lambda$ respectively. t is the thickness of the layer and λ is the wavelength of the incident monochromatic light beam; $n_{g1}$ and $n_\perp$ are refractive indices parallel and perpendicular to the optical axis, the microfibrillar direction in the case of wood fibres. The quantity $(n_\|-n_\perp)=\delta_n$ is called the birefringence of the specimen. Eq. (2) can be shown as $$T(\Delta, \theta) = e^{-j(\Delta_\|+\Delta_\perp)/2} \quad (5)$$

$$\begin{pmatrix} \cos\frac{\Delta}{2} + j\sin\frac{\Delta}{2}\cos(2\theta) & j\sin\frac{\Delta}{2}\sin(2\theta) \\ j\sin\frac{\Delta}{2}\sin(2\theta) & \cos\frac{\Delta}{2} - j\sin\frac{\Delta}{2}\cos(2\theta) \end{pmatrix}.$$

This is a Jones matrix for describing the transmission properties of a birefringent specimen with only one optical axis, such as a layer in a wood fibre shown in FIG. 1(b). A wood fibre is made of many layers of cellulosic microfibrils with different microfibril orientations, i.e., different optical axes, and different thicknesses embedded in the matrix of lignin and hemicelluloses. The combined effect of n layers is equivalent to one system with a Jones matrix [20], $$T_{comb}=T_n(\Delta_n,\theta_n)T_{n-1}(\Delta_{n-1},\theta_{n-1}) \ldots T_2(\Delta_2,\theta_2)T_1(\Delta_1,\theta_1). \quad (6)$$

A wood pulp fibre consists of two walls with each wall separated into three birefringent layers, $S_1$, $S_2$, and $S_3$. The transmission matrix for a single wall, $T_{wall}$, is $$T_{wall}=T(\Delta_{S3},\theta_{S3})T(\Delta_{S2},\theta_{S2})T(\Delta_{S1},\theta_{S1}) \quad (7)$$

where light propagates through $S_1$ layer first and $S_3$ layer last. $\theta_{S1}$, $\theta_{S2}$ and $\theta_{S3}$ are the orientations of their optical axes, and $\Delta_{S1}$, $\Delta_{S2}$ and $\Delta_{S3}$ are the relative phase retardations of $S_1$, $S_2$ and $S_3$ layers respectively:

$$\Delta s_1 = (\Delta_\| s_1 - \Delta_\perp s_1) = \frac{2\pi t s_1 \delta_n s_1}{\lambda}, \quad (8)$$

$$\Delta s_2 = (\Delta_\| s_2 - \Delta_\perp s_2) = \frac{2\pi t s_2 \delta_n s_2}{\lambda},$$

$$\Delta s_3 = (\Delta_\| s_3 - \Delta_\perp s_3) = \frac{2\pi t s_3 \delta_n s_3}{\lambda},$$

where $t_{S1}$, $t_{S2}$ and $t_{S3}$, and $\delta_{nS1}$, $\delta_{nS2}$ and $\delta_{nS3}$ are the thickness and the birefringence of microfibrils in their respective layers. The $S_1$ layer is generally considered to be comprised of several layers with fibril angle 70-80° with alternating S and Z helices. The optical behaviour of such structure is approximately equivalent to a single layer with fibril angle 90° [14, 19]; That is the fibrils of $S_1$ can be approximated to be perpendicular to the fibre axis. The $S_3$ layer is treated similarly. Therefore, $\theta_{S1}=\theta_{S3}=\pi/2$ are set. The model for describing a single wall is shown in FIG. 1(b). For $\theta_{S2}=\theta$, the fibril orientation in the $S_2$ layer, $T_{wall}$ for a single fibre wall as shown in FIG. 1(b) is $$T_{wall}\left(\Delta s_1, \Delta s_2, \Delta s_3, \theta s_1 = \frac{\pi}{2}, \theta s_2 = \theta, \theta s_3 = \frac{\pi}{2}\right) = \quad (9)$$

$$T\left(\Delta s_3, \frac{\pi}{2}\right) T(\Delta s_2, \theta) T\left(\Delta s_1, \frac{\pi}{2}\right) =$$

$$e^{-j(\Delta_\| s_1 + \Delta_\perp s_1)/2} e^{-j(\Delta_\| s_2 + \Delta_\perp s_2)/2} e^{-j(\Delta\delta_\| s_3 + \Delta_\perp s_3)/2} \begin{pmatrix} a & b \\ c & d \end{pmatrix},$$

where the matrix elements are $$a = \cos\frac{\Delta s_2}{2}\cos\left(\frac{\Delta s_1 + \Delta s_3}{2}\right) + \sin\frac{\Delta s_2}{2}\sin\left(\frac{\Delta s_1 + \Delta s_3}{2}\right)\cos(2\theta) +$$

$$j\left(\sin\frac{\Delta s_2}{2}\cos\left(\frac{\Delta s_1 + \Delta s_3}{2}\right)\cos(2\theta) - \cos\frac{\Delta s_2}{2}\sin\left(\frac{\Delta s_1 + \Delta s_3}{2}\right)\right),$$

$$b = -\sin\frac{\Delta s_2}{2}\sin(2\theta)\sin\left(\frac{\Delta s_1 - \Delta s_3}{2}\right) +$$

$$j\left(\sin\frac{\Delta s_2}{2}\sin(2\theta)\cos\left(\frac{\Delta s_1 - \Delta s_3}{2}\right)\right),$$

$$c = -b^*,$$

$$d = a^*.$$

It is assumed that for the wood pulp fibre being measured, the opposing fibre walls have the same wall thicknesses for all layers, and their microfibrils in the $S_2$ layer is wrapped around the fibre axis in a helix at an angle such that the microfibril directions of the opposing $S_2$ layers are crossed. The Jones matrix for describing the $S_2$ layer with the orientation of the optical axis, fibril angle, of $-\theta$ is $T(\Delta_{S1}, \pi/2)T(\Delta_{S2},-\theta)T(\Delta_{S3},\pi/2)$. Therefore, the Jones matrix describing an intact wood pulp fibre as shown in FIG. 1(b), consisting of two fibre walls with the same thickness, but crossed fibril angle in the $S_2$ layer, can be written as $$T_{fibre}\left(\Delta s_1, \Delta s_2, \Delta s_3, \theta s_1 = \frac{\pi}{2}, \theta, \theta s_3 = \frac{\pi}{2}\right) = \quad (10)$$

$$\left[T\left(\Delta s_1, \frac{\pi}{2}\right) T(\Delta s_2, -\theta) T\left(\Delta s_3, \frac{\pi}{2}\right)\right] =$$

$$e^{-j(\Delta_\| s_1 + \Delta_\perp s_1)} e^{-j(\Delta_\| s_2 + \Delta_\perp s_2)} e^{-j(\Delta\delta_\| s_3 + \Delta_\perp s_3)} \begin{pmatrix} a & b \\ c & d \end{pmatrix}$$

where the elements of the transmission matrix are $$a = \left\{ \begin{array}{c} [\sin^2(2\theta) + \cos(\Delta s_2)\cos^2(2\theta)]\cos(\Delta s_1 + \Delta s_3) + \\ 2\sin^2\left(\frac{\Delta s_2}{2}\right)\sin^2(2\theta)\sin(\Delta \delta s_1)\sin(\Delta s_3) + \\ \sin\Delta s_2 \cos(2\theta)\sin(\Delta s_1 + \Delta s_3) \end{array} \right\} +$$

-continued $$j\left\{ \begin{array}{c} \sin\Delta s_2 \cos(2\theta)\cos(\Delta s_1 + \Delta s_3) - \\ [\sin^2(2\theta) + \cos(\Delta s_2)\cos^2(2\theta)]\sin(\Delta s_1 + \Delta s_3) + \\ 2\sin^2\left(\frac{\Delta s_2}{2}\right)\sin^2(2\theta)\cos(\Delta s_1)\sin(\Delta s_3) \end{array} \right\},$$

$$b = -\sin^2\frac{\Delta s_2}{2}\sin(4\theta)\cos(\Delta s_3) + \sin(2\theta)\sin(\Delta s_2)\sin(\Delta s_3),$$

$$c = -b,$$

$$d = a^*.$$

For wood fibres, cellulose microfibrils show strong birefringence, but insignificant absorption in the visible light region. The matrix, containing lignin and hemicellulose, that imbeds microfibrils, has a weak absorption in the visible or longer wavelength light regions that can be neglected. In the case of measurements done at the wavelength region that absorption from the embedding matrix is significant [18], the present invention can still be applied. Since the absorption property of lignin is not dichroic, the absorption term can be decoupled from the birefringence term in the transmission matrix, e.g, $$T=T(\text{Absorption})T(\text{Birefringence matrix}). \quad (11)$$

According to the Lambert-Beer law, the absorption term, $T(\text{Absorption})=\exp(-2k(\lambda)t)$, is a scale factor that can only affect the overall intensity of the transmitted light. $k(\lambda)$ is the extinction coefficient that depends on the wavelength $\lambda$, and $t$ is the fibre wall thickness. This absorption term T(Absorption) can be determined by the unpolarized transmission light at the defined wavelengths or can be determined from $k(\lambda)$ and the wall thickness for proper evaluations of birefringence of the specimen. For specimens with very weak absorption, such as absorption of wood fibres in the visible light region, T(Absorption) is set to be one. Even with unknown absorption in the measured samples, the results, particularly for the fibre wall thickness measurements, will not be affected because measurements of this method depend strongly on the relative multi-wavelength intensities as discussed later.

Circularly Polarized Light System

A circularly polarized light system such as dark- or bright-field circularly polarized light system is used to realize this measurement principle. This measurement system is independent of specimen orientations because the light is circularly polarized. Moreover, a novel, comparatively simple solution for determining the relative phase retardation and the fibril angle in such a polarized light system is developed for an intact fibre with two opposite walls that have the same thickness, but a crossed fibril angle $\theta$ in the $S_2$ layer.

Figure 2:
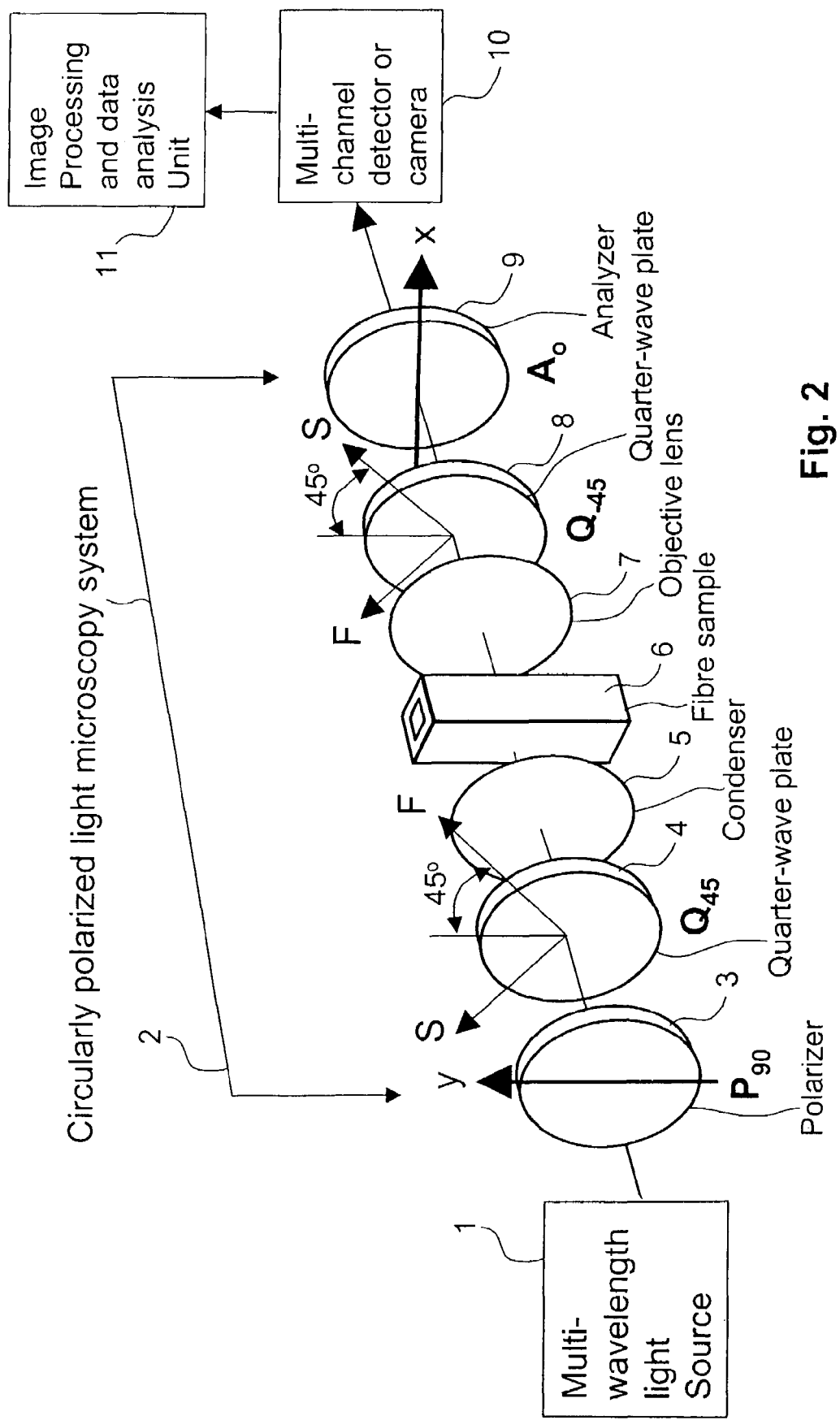
FIG. 2 shows a schematic diagram of a system for determining the thicknesses and optical axes of multi-layered specimens, such as wall thickness and fibril angle of intact wood fibres.

A combination of a properly oriented linear polarizer and a quarter-wave retarder will form a circular polarizer. FIG. 2 schematically illustrates a device in accordance with this invention, describing a circularly polarized light microscopy (CPLM) system with a pulp wood fibre inserted as a sample. The device comprises a multi-wavelength light source unit 1, a circularly polarized light system with appropriate imaging optics 2, a multi-channel detector or camera 10 that detects the multi-wavelength light intensities, and image processing and data analysis unit 11.

A circularly polarized light system consists of a pair of polarizers: a linear polarizer P 3 and analyzer A 9, and in between the polarizers are two well-matched precision achromatic quarter-wave retarders $Q_{45}$ 4 and $Q_{-45}$ 8 with their optical (fast) axes F oriented 90 degrees to each other and 45 degrees to the polarizers as shown. The CPLM is a dark-field system when the two polarizers are crossed as shown in FIG. 2, but a bright-field system when the two polarizers are parallel. To satisfy the accuracy requirements of the measurements, two precision achromatic quarter-wave retarders with retardance $\lambda/4\pm\lambda/100$ are required, and the pair are matched to within $\lambda/200$ retardance at any predetermined wavelength. The sample 6 can be placed on a stage for static measurements, or can be passing through a fibre flow-through system as in the existing commercial fibre length analysers. The fibre sample 6 under investigation is placed between two circular polarizers. The incident circularly polarized light is focused on the sample 6 through the condenser 5 and the sample to be measured is magnified and imaged by an objective lens 7 suitable for polarized light application. The multi-wavelength images are captured by a multi-channel digital camera such as a color charge-coupled device (CCD) camera 10, or other appropriate optics and detectors for the chosen wavelengths. The transmitted light intensities of different wavelengths will be analysed for determining the relative phase retardation and the orientations of optical axes of the specimen under study, such as wall thickness and fibril angle in wood fibres, according to the novel solutions described below.

Figure 3:
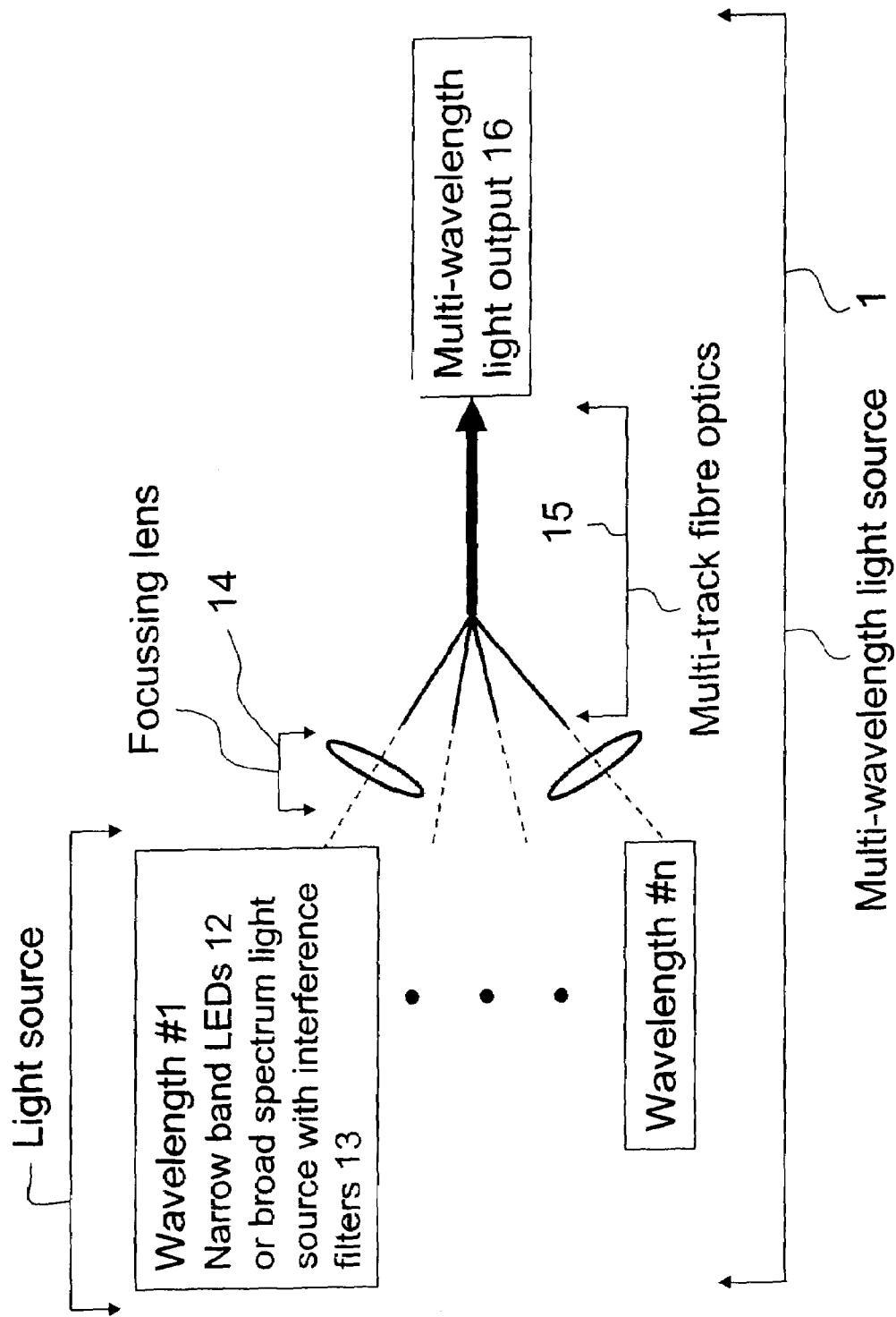
FIG. 3 shows a schematic diagram for a multi-wavelength light source, which consists of numerous predetermined and well-defined single wavelengths.

The light source unit 1, as shown in FIG. 3, provides incident light of numerous predetermined and well-defined single wavelengths to the system. These single wavelengths are chosen so that they are well separated, but they must still be within the acceptable working wavelength range of the pair of achromatic quarter-wave retarders chosen for the system. For instance, a pair of retarders used for experiments in this invention had a working wavelength range from 450 nm to 640 nm. Three wavelengths 450, 540 and 640 nm were chosen for the incident light beam. The multi-wavelength light source unit 1 can be comprised of lasers or numerous light emitting diodes (LEDs) 12, each having a well-defined single wavelength emission. It can also be a broad spectrum light source with a set of narrow band pass interference filters 13 with each filter having a well-defined wavelength. The different light sources are coupled to the inputs of the multi-track fibre optics 15 by focussing lenses 14. The multi-wavelength light sources are then guided into a single light source at the output of the fibre optics 16.

According to the Jones calculus, the Jones matrices for polarizer P and analyzer A, shown in FIG. 2, are $$P = \begin{bmatrix} 0 \\ 1 \end{bmatrix}, \text{ and } A = [1 \ 0], \quad (12)$$

and the matrices for the quarter-wave retarders' fast axes oriented at 45 and −45 degrees are [21]

$$Q_{45°} = \frac{j+1}{2}\begin{bmatrix} 1 & j \\ j & 1 \end{bmatrix}, Q_{-45°} = \frac{j+1}{2}\begin{bmatrix} 1 & -j \\ -j & 1 \end{bmatrix} \quad (13)$$

The electric-field vector E of the light beam that emerges from the analyzer, for the case of the dark-field circularly polarized light system shown in FIG. 2, with a sample inserted that is described by the matrix T, is $$E = \begin{bmatrix} E_x \\ E_y \end{bmatrix} \quad (14)$$

$$= \sqrt{I_o} \, A Q_{-45°} T Q_{45°} \begin{bmatrix} 0 \\ 1 \end{bmatrix}$$

$$= \sqrt{I_o} \begin{bmatrix} 1 & 0 \\ 0 & 0 \end{bmatrix} \frac{j+1}{2}\begin{bmatrix} 1 & -j \\ -j & 1 \end{bmatrix} \begin{bmatrix} a & b \\ c & d \end{bmatrix} \frac{j+1}{2}\begin{bmatrix} 1 & j \\ j & 1 \end{bmatrix} \begin{bmatrix} 0 \\ 1 \end{bmatrix}$$

$$= \sqrt{I_o} \left(\frac{j+1}{2}\right)^2 [j(a-jc)+(b-jd)]\begin{bmatrix} 1 \\ 0 \end{bmatrix},$$

where $I_o$ is the intensity of the light incident on the specimen, which can be determined when no sample is inserted under the arrangement of bright-field circular polarized light system (parallel polarizer 3 and analyzer 9 described in FIG. 2). The transmitted light intensity under the dark-field circular polarized light system, $I_{dark}$, can be obtained as follows:

$$I_{dark} = E_x * E_x + E_y * E_y = I_o(a_2^2 + b_2^2). \quad (15)$$

where $a_2$, $b_2$ are the imaginary parts of the elements a, b respectively.

Similar to the dark-field case, the present invention can also be easily realized in the bright field circularly polarized light system. In this case, the transmitted light intensity, $I_{bright}$, is $$I_{bright} = I_o(a_1^2 + b_1^2). \quad (16)$$

where $a_1$, $b_1$ are the real parts of the elements a, b respectively. The bright- and dark fields are inversion of each other.

The response of various types of specimens can be evaluated under dark-field circularly polarized light system. For instance, if a specimen has $\Delta$ relative phase retardation and $\theta$ optical axis, the transmitted light intensity is [21]

$$I_{single\ layer,dark}(\Delta, \theta) = I_o \sin^2 \frac{\Delta}{2}, \quad (17)$$

where the elements $a_2, b_2$ in the matrix of the Eq. (5) are used. The intensity depends only on $\Delta$ but not on $\theta$ because the specimen is under circularly polarized light system.

For a multi-layered specimen, such as a single fibre wall with $S_1$, $S_2$ and $S_3$ layers with $\Delta_{S1}$, $\Delta_{S2}$ and $\Delta_{S3}$ relative phase retardations, and $\theta$ optical axis in the $S_2$ layer, the transmitted light intensity is $$I_{wall,dark}(\Delta s_1, \Delta s_2, \Delta s_3, \theta) = I_o \sin^2 \frac{\Delta s_2}{2} \quad (18)$$

$$\left\{ \begin{array}{l} \left(\cos^2\left(\frac{\Delta s_1 + \Delta s_3}{2}\right)\cos^2(2\theta) + \cos^2\left(\frac{\Delta s_1 - \Delta s_3}{2}\right)\sin^2(2\theta)\right) + \\ \cos^2 \frac{\Delta s_2}{2}\sin^2\left(\frac{\Delta s_1 + \Delta s_3}{2}\right) - \frac{1}{2}\cos(2\theta)\sin(\Delta s_2)\sin(\Delta s_1 + \Delta s_3) \end{array} \right\}$$

where the elements $a_2$, $b_2$ in the matrix of the Eq. (9) are used. If both $\Delta_{S1}$ and $\Delta_{S3}$ are set to zero, the intensity for a single layer is obtained, and Eq. (18) is reduced to Eq. (17).

For an intact wood pulp fibre with two opposite walls with the same thicknesses in $S_1$, $S_2$ and $S_3$ layers, but $\pm\theta$ optical axis, such as fibril angle in the $S_2$ layer of wood fibre, the transmitted light intensity is $$I_{fibre,dark}(\Delta s_1, \Delta s_2, \Delta s_3, \theta) = \qquad (19)$$

$$I_o \begin{pmatrix} \sin(\Delta s_2)\cos(2\theta)\cos(\Delta s_1 + \Delta s_3) - \\ [\sin^2(2\theta) + \cos(\Delta s_2)\cos^2(2\theta)]\sin(\Delta s_1 + \Delta s_3) + \\ 2\sin^2\left(\frac{\Delta s_2}{2}\right)\sin^2(2\theta)\cos(\Delta s_1)\sin(\Delta s_3) \end{pmatrix}^2$$

where the elements $a_2, b_2$ in the matrix of the Eq. (5) are used. This equation has four unknown parameters: $\Delta_{S1}$, $\Delta_{S2}$, $\Delta_{S3}$ and $\theta$ to be determined. The $S_3$ layer is known to be very thin (<0.01 μm) [1, 14, 19, 23], therefore the last term in the above equation is negligible compared to the first two terms. Therefore, the relative phase retardations of $S_1$ and $S_3$ layers can be approximately treated as one unknown parameter $\Delta_{S1} + \Delta_{S3}$. This will reduce the unknown parameters to three. In order to determine the three unknown parameters, a minimum of three different predetermined wavelengths are required in the incident light beam so that the transmitted light intensities, $I_{fibre,\ dark}$, at three different wavelengths can be measured simultaneously for a wood fibre under study. The three unknown parameters can then be determined by best fitting Eq. (19) to the $I_{fibre,\ dark}$ data, and hence fibre's wall thickness and fibril angle $\theta$ can be determined from the fit. Eq. (19) will be used for analysing fibre properties of an intact wood fibre.

It is interesting to note that if the $S_1$ and $S_3$ layers are neglected, and only two opposite $S_2$ layers in the fibre are considered as in Ye et al. [15, 16, 18] and Ye [P2, 17], then Eq. (19) becomes $$I_{fibre,\ dark}(\Delta_{S1}=0, \Delta_{S2}, \Delta_{S3}=0, \theta) = I_o \sin^2 \Delta_{S2} \cos^2(2\theta) \qquad (20)$$

Compared to the corresponding expressions derived in the linear polarized light case [P2] or Mueller matrix polarimetry [17], this equation that relates the transmitted light intensity to $\Delta_{S2}$ and $\theta$ for an intact fibre is unexpectedly simple. If the effects of the $S_1$ and $S_3$ layers are taken into considerations, the expressions in the methods described by Ye et al. [15, 16, 18] and Ye [P2, 17] are expected to be more complex compared to the Eq. (19) in the present invention. Therefore, interpretation of the data will be more complex and extraction of reliable measurements is uncertain.

As described in Eq. (4), the relative phase retardations $\Delta_{S1}$, $\Delta_{S2}$ and $\Delta_{S3}$ in the $S_1$, $S_2$ and $S_3$ layers depend on $t_{S1}\delta_{nS1}$, $t_{S2}\delta_{nS2}$ and $t_{S3}\delta_{nS3}$, the product of thickness and birefringence of microfibrils in their respective layers. The birefringences of these layers, related to their chemical composition and degree of molecular orientation, are assumed to be similar, so that $\delta_{nS1} = \delta_{nS2} = \delta_{nS3} = \delta_n$ [14, 19]. They are further assumed to be a constant for fibres in the same species' pulps subjected to similar pulping and papermaking treatments. For some species, their birefringences are shown to be similar by Page et al. [19]. The birefringence $\delta_n = (n_\parallel - n_\perp)$ of the microfibrils is found to be 0.04-0.06 for most pulp fibres [19, 22].

Figure 4A:
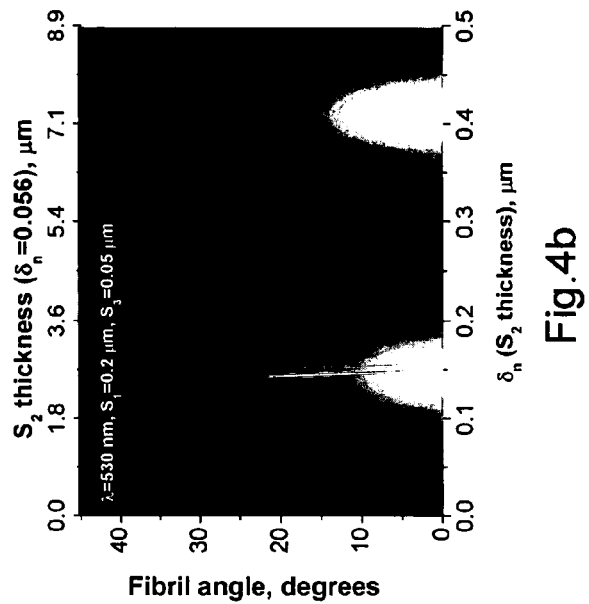
FIGS. 4(a), (b) and (c) show theoretical intensity maps for various $δ_n·ts_2$ and fibril angle of an intact fibre imaged under a dark-field circularly crossed-polarized light system. Three intensity maps with different incident light wavelengths (a) 450, (b) 530 and (c) 640 nm are generated according to Eq. (19) when the thicknesses of $S_1$ and $S_3$ are set to be 0.2 and 0.05 μm respectively. The scale on the top x-axis is plotted as the $S_2$ layer thickness, $ts_2$, when the birefringence, $δ_n$, is set to 0.056.
Figure 4B:
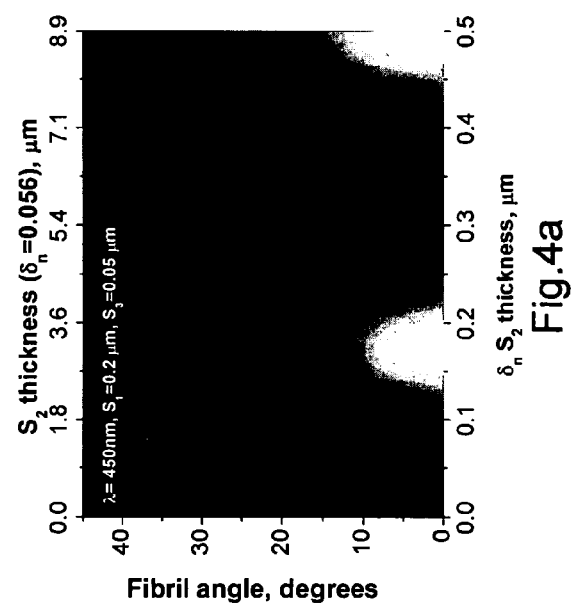
Figure 4C:
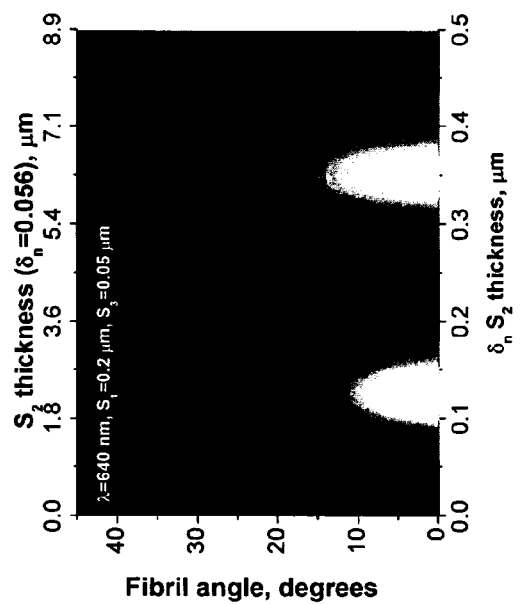

FIG. 4 shows theoretical transmitted intensity maps of three wavelengths (a) 450, (b) 530 and (c) 640 nm as a function of $\delta_n t_{S2}$ and fibril angle of an intact fibre in dark-field CPLM system. They are generated according to Eq. (19), and the thicknesses for $S_1$ and $S_3$ layers are set to be 0.2 and 0.05 μm respectively—typical mean thicknesses of $S_1$ and $S_3$ layers for most softwood fibres [1, 14, 19, 23]. The scale of the top x-axis is plotted as the thickness of $S_2$ layer, $t_{S2}$, when the birefringence, $\delta_n$, is set to 0.056 for chemical pulp fibres [19]. This illustrates graphically that wood fibres with different wall thicknesses and fibril angles are associated with different transmitted intensities at different wavelengths. Therefore, by matching the transmitted intensities to the intensity maps of various wavelengths in FIG. 4, fibre wall thickness and fibril angle can be determined accurately and uniquely. "Matching" here means the best non-linear fitting of Eq. (19) to the measured intensities.

Figure 5:
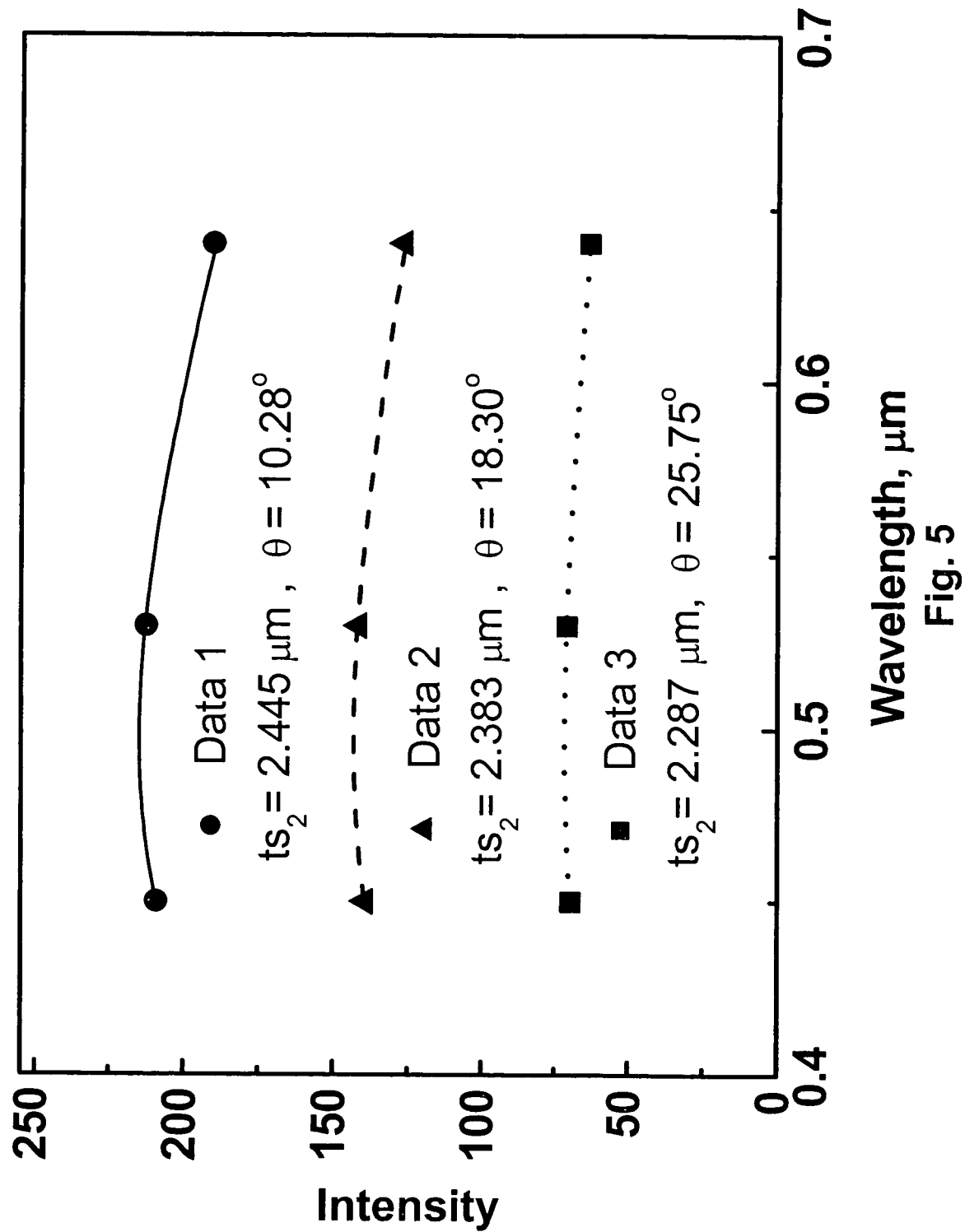
FIG. 5 shows three data sets with different intensities but the same relative intensities among different wavelengths. The data in this graph follow the criteria set for $δ_n$, $S_1$ and $S_3$ in FIG. 4. The lines shown are the intensities as function of wavelength according to Eq. (19).
Figure 6A:
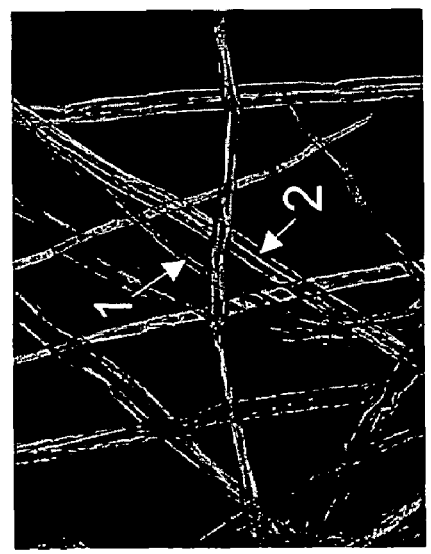
FIGS. 6(a), (b), (c), (d), (e) and (f) show micrographs of unbleached Douglas fir and western red cedar chemical pulp fibres imaged in the dark-field CPLM system with wavelengths 450, 530 and 640 nm. Micrographs (a), (b) and (c) are images of wet fibres immersed in water, and (d), (e) and (f) are images of the same fibres after drying. The two marked locations will be used to illustrate the present method for determining wall thickness and fibril angle.
Figure 6D:
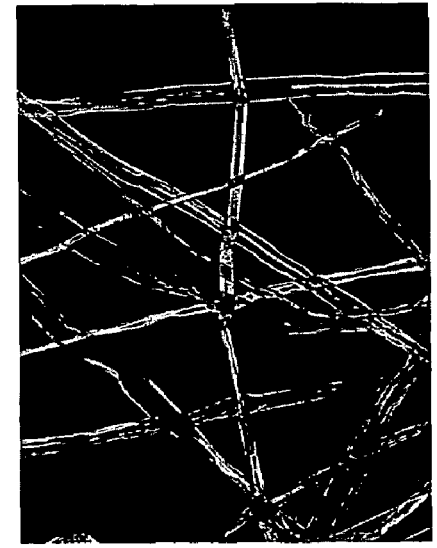
Figure 6B:
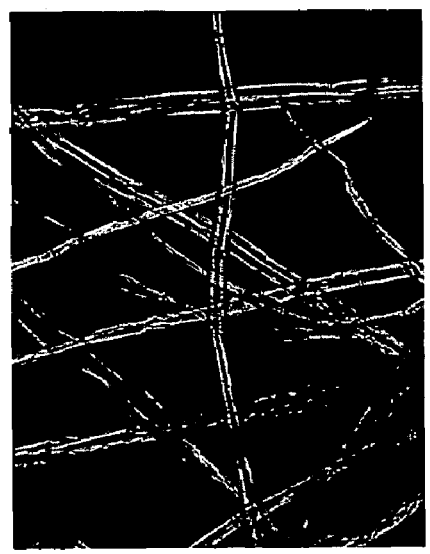
Figure 6E:
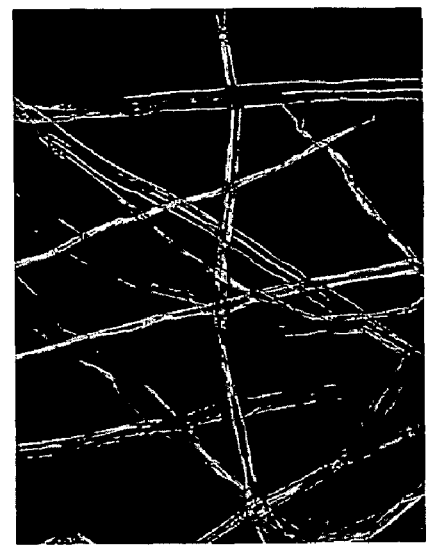
Figure 6C:
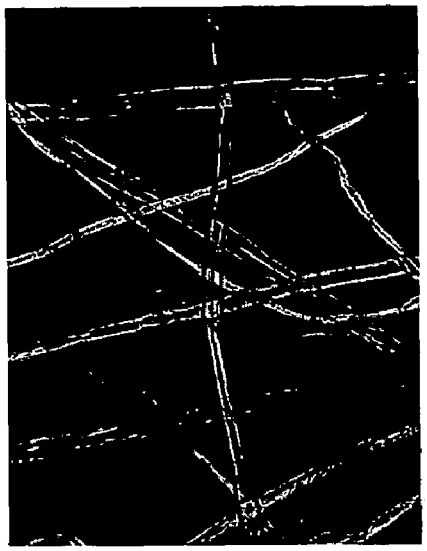
Figure 6F:
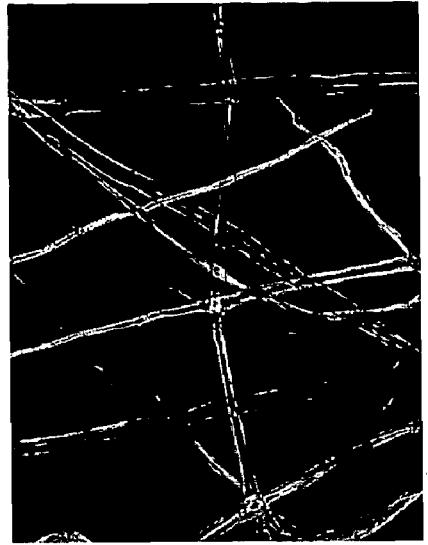

It is important to note in the intensity maps of FIG. 4 that while fibril angle depends more on the overall transmitted intensities, the fibre wall thickness measurement depends more on the relative transmitted intensities at various wavelengths. If the three intensity maps of 450 nm (red), 530 nm (green), and 640 nm (blue) in FIG. 4 are merged to form a color map, fibres with similar fibre wall thickness are more or less associated with the same color, regardless of their fibril angles. This can be further illustrated in FIG. 5, showing three data sets with different intensities but the same relative intensities among different wavelengths. The data set 1 has one-and-half times higher intensities than data set 2, and three times higher than data set 3. While these three data sets correspond to different fibril angles, which increase as intensities decrease, they correspond to similar wall thicknesses for $S_2$ layer ($t_{S2}$), 2.445, 2.383 and 2.287 μm as shown. This demonstrates the robustness of the present technique for measuring fibre wall thickness because other optical phenomena, such as light absorption that reduces the transmitted light intensity, will not really affect the accuracy of the measurements. The robustness of the technique has been confirmed through many examples, and some will be discussed below.

FIG. 6 shows micrographs of wet and dried unbleached mixture of Douglas fir and western red cedar chemical pulp fibres imaged in dark-field CPLM system with wavelengths 450, 530 and 640 nm. These micrographs were taken with a 10× objective lens with a numerical aperture of 0.25 (N.A.=0.25). FIGS. 6(a), (b) and (c) are micrographs of wet fibres immersed in water, and FIGS. 6(d), (e) and (f) are micrographs of the same fibres after drying—the dried fibres were mounted in immersion oil, minimizing light scattering in the dry fibre sample, before these micrographs were taken. It is evident that the corresponding wet and dry fibres, taken at the same wavelength, are shown to have very similar intensities as shown in these micrographs. This strongly indicates that the measurements should be the same whether they are done in wet or dry conditions as demonstrated next.

Figure 7:
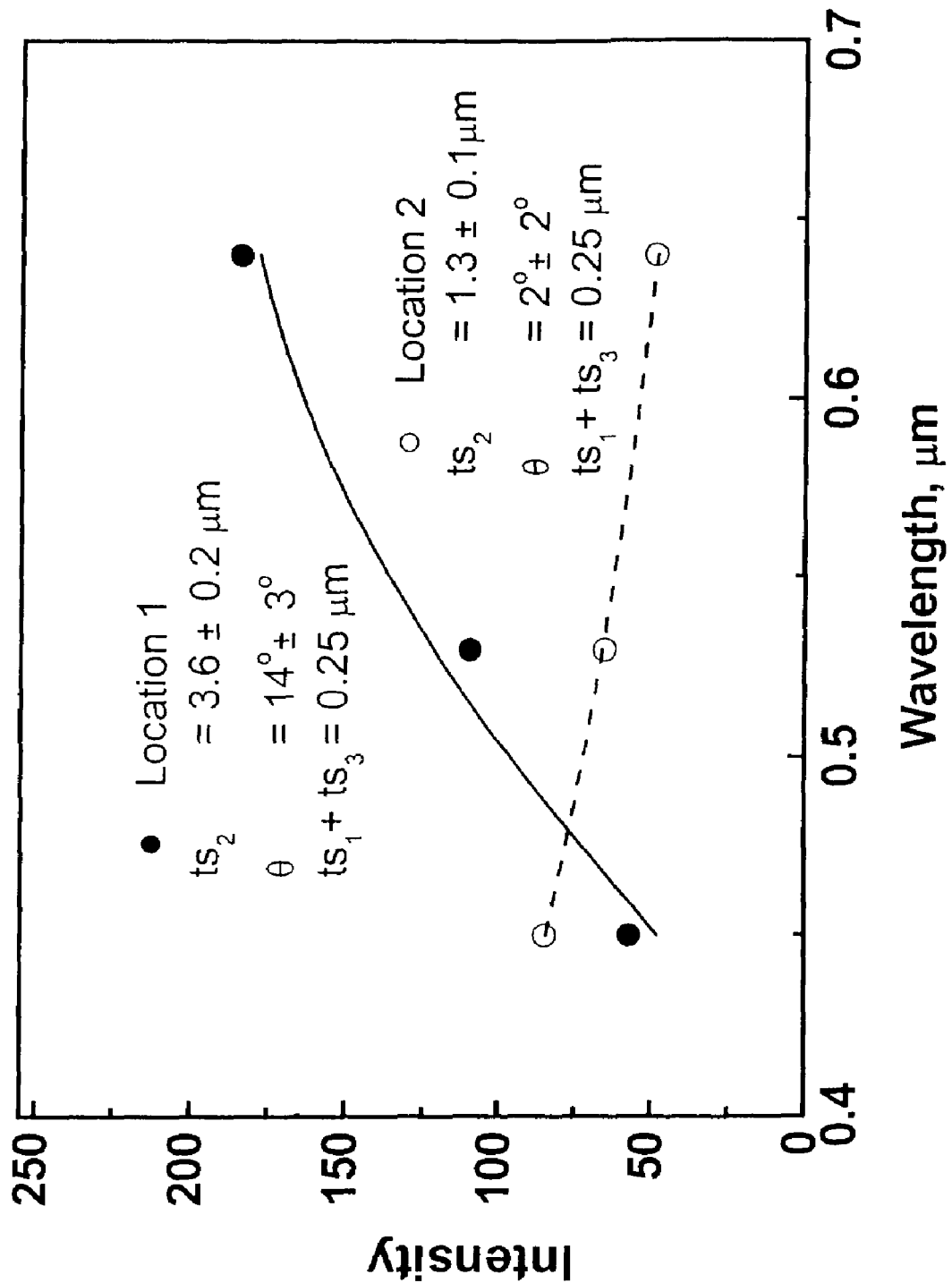
FIG. 7 plots the transmitted light intensities versus three wavelengths 450, 530 and 640 nm for locations 1 and 2 marked in FIG. 6(a). The wall thickness and fibril angle for these two locations in the fibres are determined from the best fits, as shown, of Eq. (19) to these data. The birefringence and the thickness of $S_1+S_3$ are set to 0.0553 and 0.25 μm respectively.

Two marked locations in the two fibres shown in FIG. 6 are used to demonstrate how the wall thickness and fibril angle can be determined from the light intensities of different wavelengths obtained from the dark-field CPLM system. The intensities of these two areas versus wavelength are plotted in FIG. 7. The three parameters $t_{S2}$, $\theta$ and $t_{S1}+t_{S3}$ are determined by the non-linear fitting of Eq. (19) to the intensity data at three wavelengths. The best fits shown in this figure were obtained by setting $\delta_n = 0.0553$ [19] and $t_{S1}+t_{S3} = 0.25$ μm [1, 14, 19, 23], values normally found in softwood chemical pulp fibres. The fibre wall thickness is then calculated as $t_{S1}+t_{S3}+t_{S2}$. The wall thickness and fibril angle for location 1 are found to be 3.9±0.2 μm and 14±3°, and for location 2 are found to be 1.6±0.1 μm and 2±2°.

Figure 8:
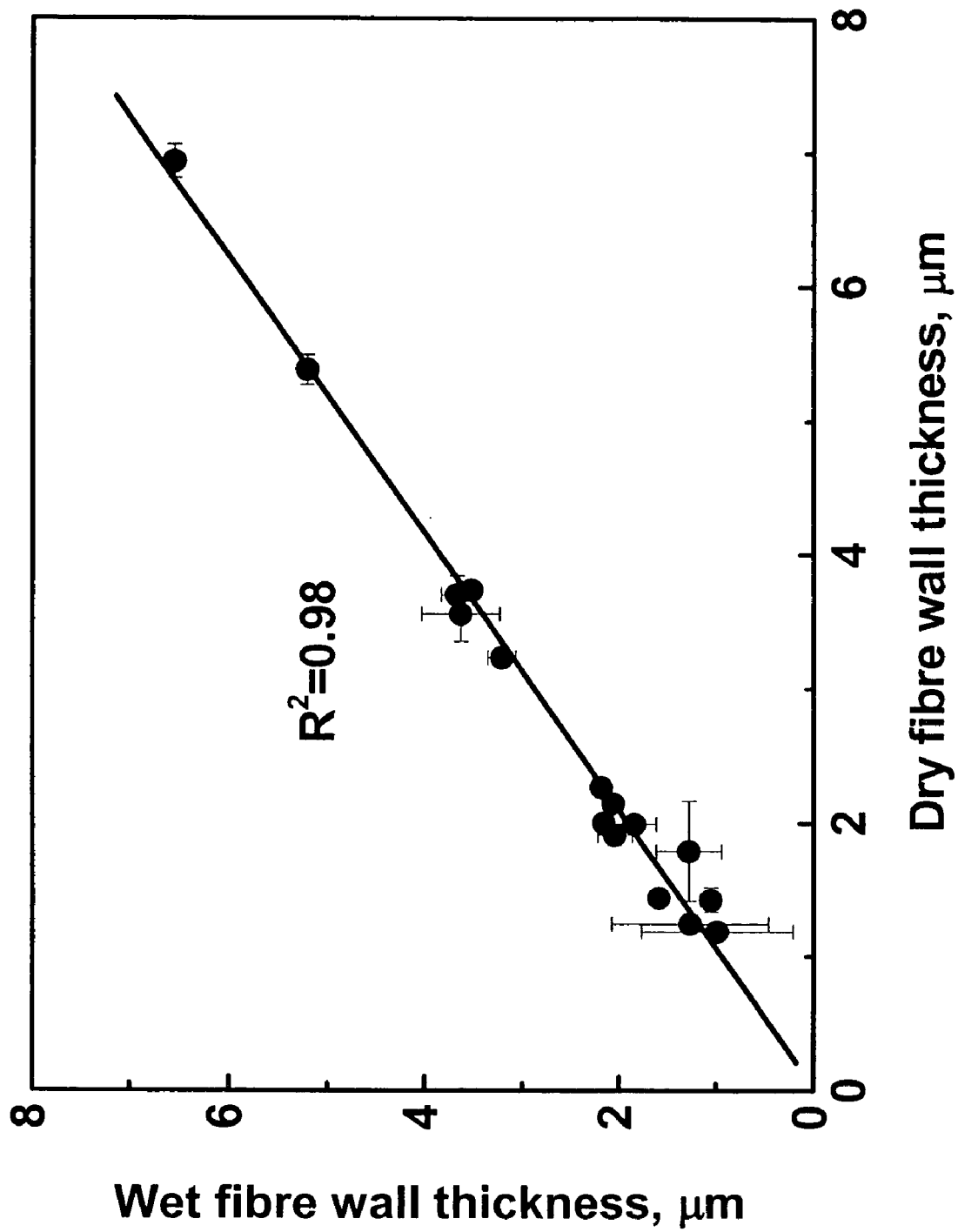
FIG. 8 compares the wall thicknesses determined from the same wet and dry wood fibres shown in FIG. 7. The coefficient of determination $R^2$ of 0.98 shows a strong correlation between the measurements taken from wet and dry fibres.

Many different locations of wet and dry fibres shown in FIG. 6 were evaluated for their wall thicknesses and fibril angles. FIG. 8 compares the wall thicknesses determined from the corresponding areas in the micrographs of the same wet and dry fibres. All measurements were done at the middle regions of the fibres. Strong correlation between the measurements from the wet and dry fibres is shown, and the coefficient of determination $R^2$ of 0.98 was found. This confirms strongly that the present invention provides similar wall thickness measurements either from wet or dry wood fibres. It demonstrates the robustness of this method in that similar results can be obtained from the less light scattering dry fibres in immersion oil and the more light scattering wet fibres in water.

FIG. 9(a) shows three micrographs with wavelengths 450, 530 and 640 nm of a small fibre segment of a thick-walled Douglas fir chemical pulp fibre in dark-field CPLM system imaged with a 40×, N.A.=0.65 objective lens. FIG. 9(b) shows a cross-sectional image of the fibre segment in FIG. 9(a) generated non-destructively by using confocal laser scanning microscopy. The double wall thickness, 2 ($t_{S1}+t_{S2}+t_{S3}$), was determined across a location in the fibre segment with $\delta_n$=0.0553 and $t_{S1}+t_{S3}$=0.25 µm [1, 14, 19, 23] from the micrographs shown in FIG. 9(a). The vertical thickness across the fibre was determined from the confocal cross-sectional image in FIG. 9(b). These two wall thickness profiles are shown in FIG. 9(c). These two techniques for measuring wall thickness agree very well, particularly for flat areas. This strongly supports the validity of the CPLM technique for determining wall thickness of wood fibres. Relatively poorer agreement results from areas where fibre edges occur. This can be explained by the strong light scattering occurring at areas with edges. Therefore, to minimize the influence and effects of light scattering from the edges in fibre wall, in particular if the fibre being measured is immersed in the water, the measurement is best done at the flat region or the middle region of a fibre. Flat areas can be easily recognized by the uniformly distributed intensities in the CPLM images, implying similar wall thickness in these areas.

Figure 10:
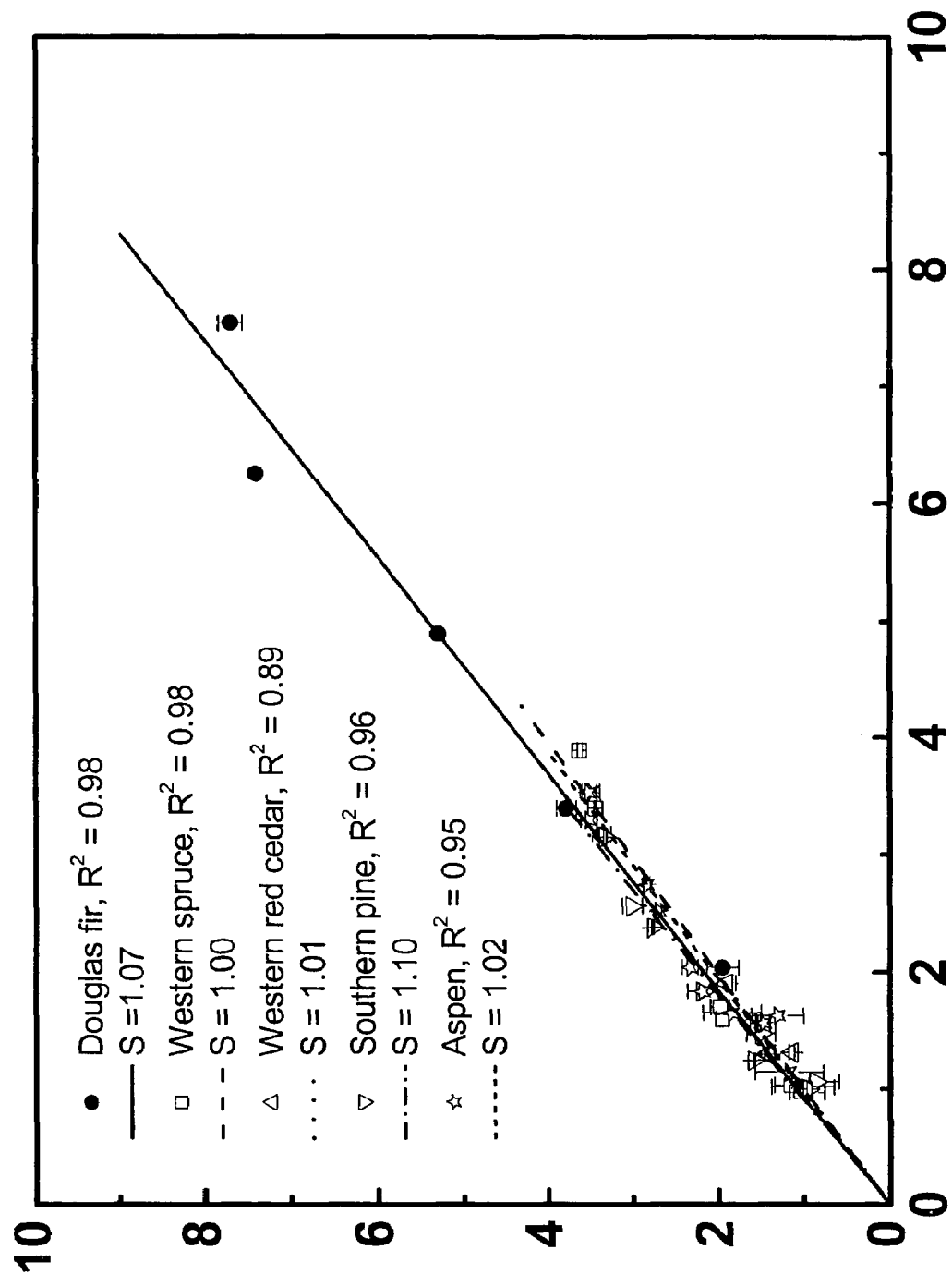
FIG. 10 shows the fibre wall thickness measured from the confocal cross-sectional images versus the measurements determined from the CPLM method for various unbleached and bleached chemical pulp fibres. The linear fits are also shown, and their slopes, S, are found to be close to one for all data.

FIG. 10 shows the fibre wall thickness measured from the confocal cross-sectional images versus the fibre wall thickness measurements determined from the CPLM method for a variety of chemical pulp fibres. Douglas fir, western red cedar and western spruce are unbleached chemical pulp fibres of three different softwood species, whereas softwood, southern pine, and a hardwood, aspen, are fully bleached. All CPLM micrographs were generated using a 10× objective lens with N.A.=0.25, and the same birefringence property $\delta_n$=0.056 [19] was used to determine the wall thickness of all fibre samples by using the CPLM method described in the present invention. The data shown in FIG. 10 clearly demonstrate strong correlations between the present invention, the new CPLM method, and the well-established CLSM method [9] for the fibre wall thickness measurements. Moreover, the slopes of the linear fits, which relate these two measurements, are shown to be around one, demonstrating that the birefringence is very similar and $\delta_n$=0.056 is suitable for many types of wood pulp fibres. This clearly demonstrates the accuracy, robustness and readiness of the present invention for measuring wall thickness of various kinds of wood fibres.

Figure 11:
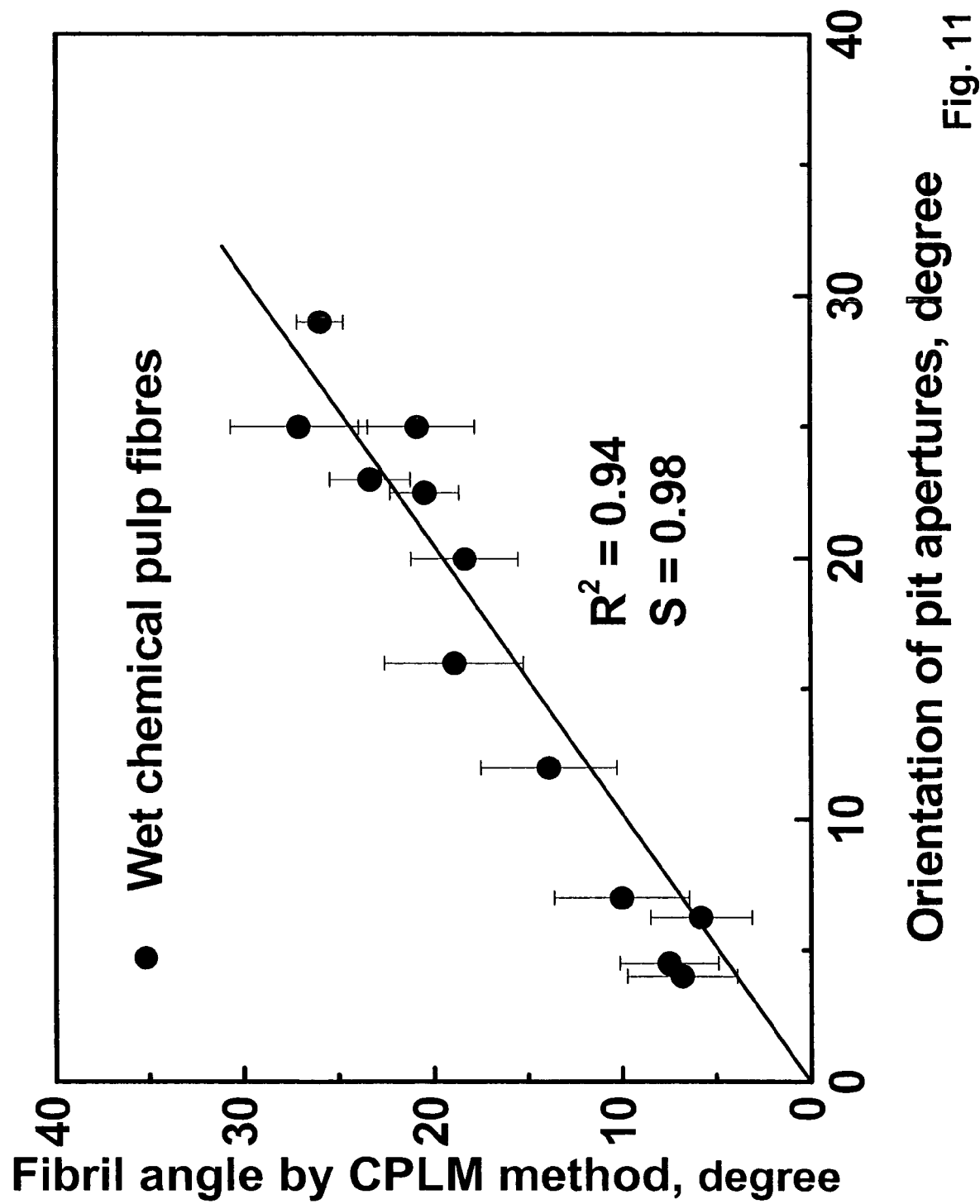
FIG. 11 shows the orientation of the pit apertures versus the fibril angle measured by the CPLM method for wet chemical pulp fibres.

Measurements of the angle between the fibre axis and the major axis of elongated pit apertures has been used for approximating the fibril angle of the $S_2$ layer in the fibre wall [13]. The orientation of the pit apertures in wet black spruce chemical pulp fibres was measured using transmitted light microscopy. The fibril angle of these fibres was also determined by the present CPLM method. The results from these two methods are compared in FIG. 11. In spite of the difficulty involved in determining accurately the orientation of pit apertures as the fibril angle, and the CPLM measurements done in flat areas away from those pits, the correlation, $R^2$=0.94, between these two methods is considered high. Moreover, the slope of the linear fit is found to be 0.98. This supports the validity of the method for measuring fibril angle of wood fibres.

The present method can also be applied to mechanical pulp fibres. Unlike chemical wood pulp fibres, mechanical wood pulp fibres have a much higher yield and retain most of the amorphous matrix of hemicelluloses and lignin. Moreover, fibre walls are altered during mechanical refining. The higher lignin content in the fibres can increase the light absorption, and the refining effects, such as external fibrillation, can create undue light scattering. Applying the present method to mechanical pulp fibres can be a challenge. In the absence of light absorption and scattering, the dark- and bright fields are inversions of each other as shown in Eq. (16). However, if light absorption and scattering are present, they have opposite effects on the dark- and bright-field CPLM intensities:

$$I_{dark}=k \cdot I_{dark}(\text{Birefringence}),$$

$$I_{bright}=k \cdot I_{bright}(\text{Birefringence})=k \cdot (I_o-I_{dark}(\text{Birefringence})), \quad (21)$$

where k is the factor for the effects of light absorption and scattering, and its value equals one if they are negligible. $I_{dark}$(Birefringence) and $I_{bright}$(Birefringence) are the transmitted light intensities under dark- and bright-field CPLM systems when only the birefringent property of a specimen is taken into account.

Figure 12B:
FIGS. 12(a) and (b) show micrographs of typical black spruce mechanical pulp fibres imaged in the dark- and bright-field CPLM systems with wavelength 530 nm, while fibres were immersed in water. These fibres were from the long fibre length fraction.
Figure 12A:
Figure 13B:
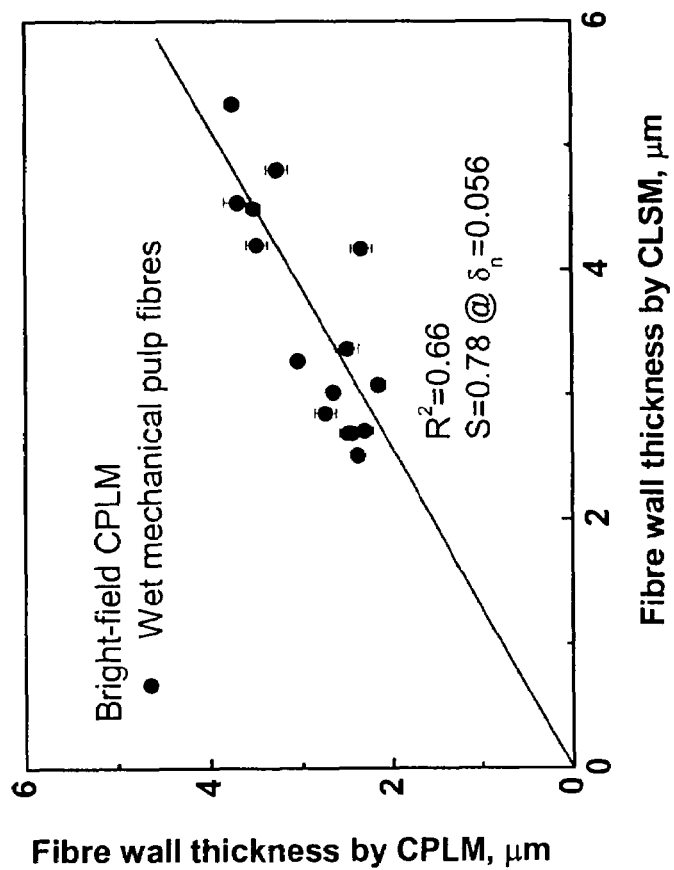
FIGS. 13(a) and (b) show the fibre wall thicknesses of mechanical pulp fibres determined from the dark- and bright-field CPLM methods versus measurements determined from the confocal cross-sectional images. The linear fits are also shown, and their slopes are found to be lower than one.
Figure 13A:
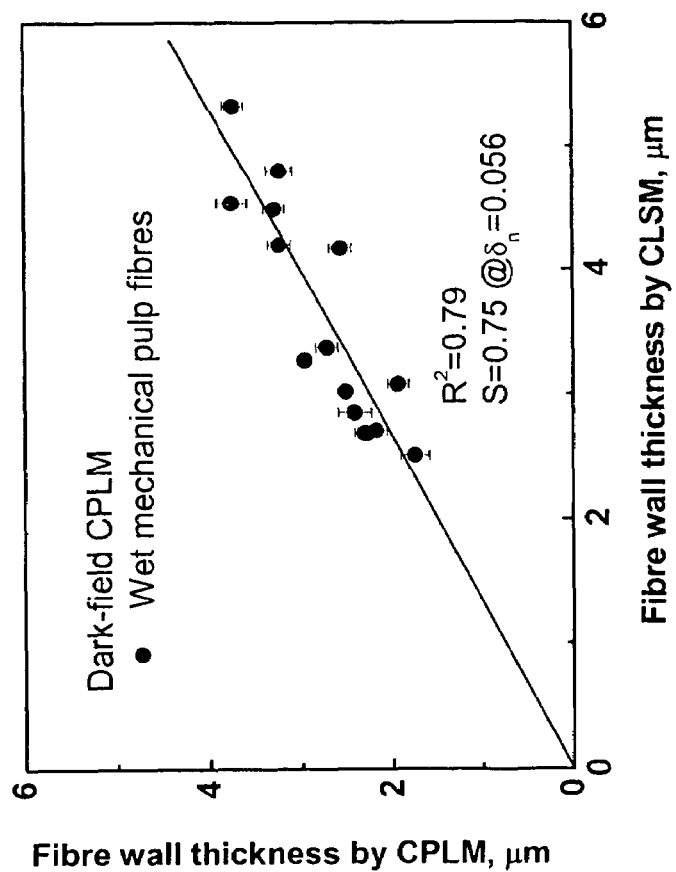

FIG. 12 shows micrographs of wet black spruce mechanical pulp fibres imaged in (a) dark-field and (b) bright-field CPLM at wavelength 530 nm. FIG. 13 shows the fibre wall thickness measured from the confocal cross-sectional images versus the measurements determined from (a) the dark-field and (b) the bright-field CPLM methods for the fibres shown in FIG. 12. Despite the complexity of mechanical wood pulp fibres, both graphs still show good correlations between dark- and bright-field CPLM and CLSM measurements. These results demonstrate that this method for measuring mechanical pulp fibre wall thickness is still far superior compared to the only commercially available instrument, the Kajaani FibreLab, which produces very poor correlation [7]. With $\delta_n$=0.056 set, the slopes for dark- and bright-fields are found to be 0.75 and 0.78 respectively. The slopes differ from one—a value found in chemical wood pulp fibres. The lower slopes reflect the fact that the present method only measures the amount of cellulosic microfibrils in the fibre wall, and not the amorphous matrix of hemicelluloses and lignin which constitutes the additional thickness of the fibre wall in mechanical wood pulp fibres. The difference of 0.03 in the slope is found in the dark- and bright-field CPLM measurements, reflecting the effects of light absorption and scattering in the fibres on the measurements. Such a small difference demonstrates and confirms that the CPLM measurements are not affected strongly by light absorption and scattering.

The factor k in Eq. (21) can be obtained from an unpolarized light transmission. On the other hand, if both dark- and bright-field CPLM measurements are done simultaneously, the k can also be obtained from $$k=(I_{dark}+I_{bright})/I_o. \quad (22)$$

Figure 14:
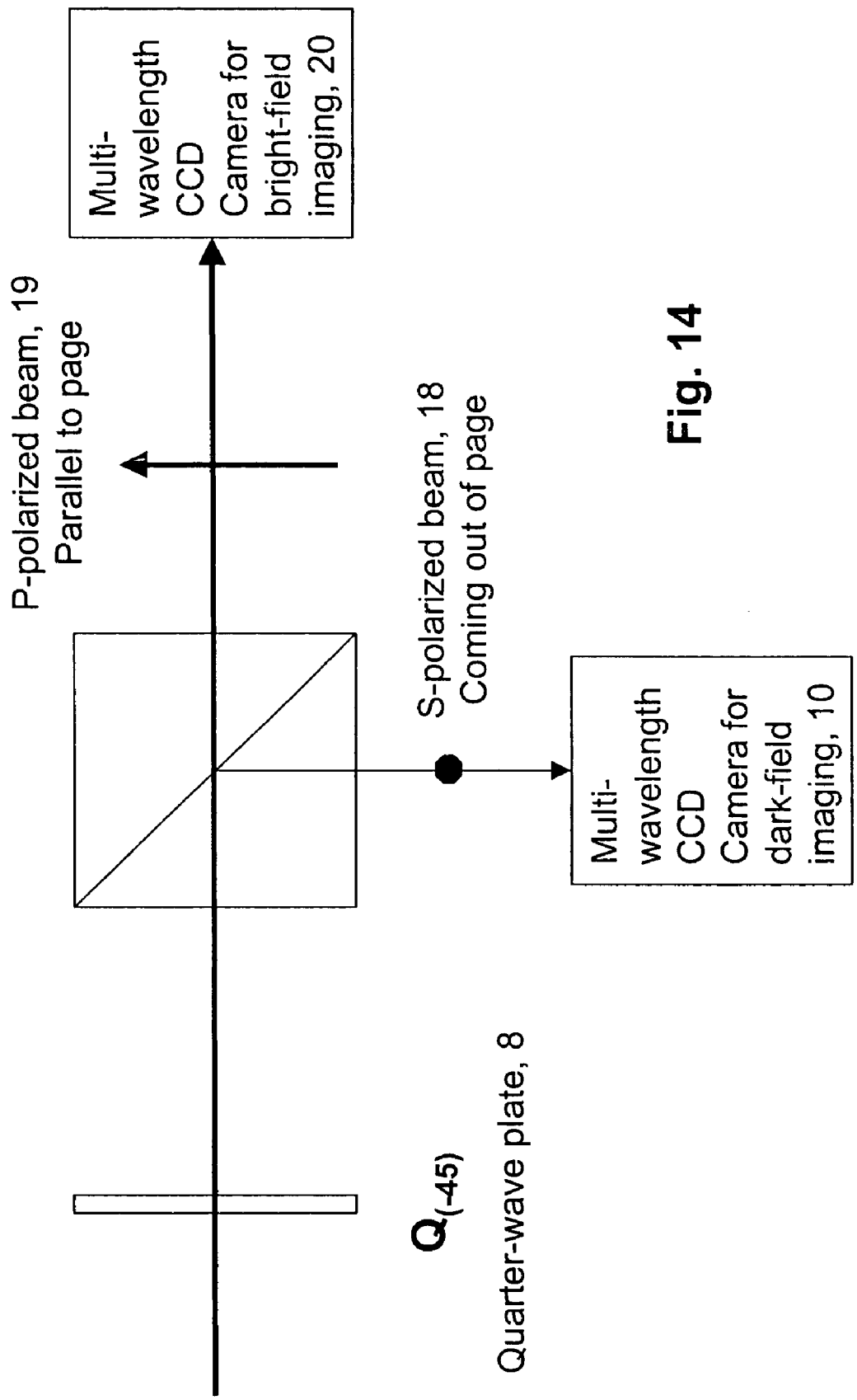
FIG. 14 shows a schematic diagram for the last part of a system described in FIG. 2 that allows simultaneous measurements of dark- and bright-field CPLM methods.
Figures 15A, 15B:
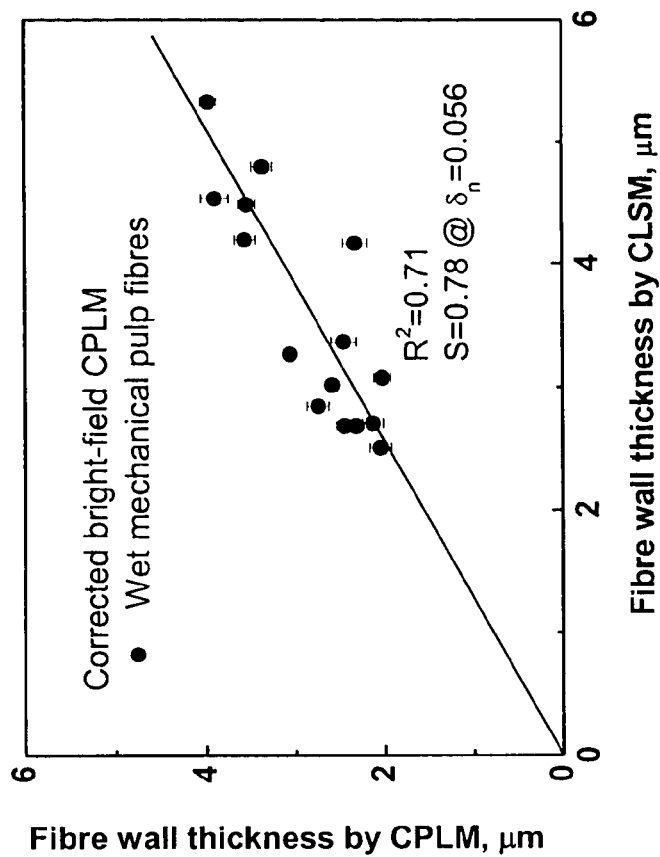
FIGS. 15(a) and (b) show the corrected fibre wall thicknesses determined from the dark- and bright-field CPLM methods versus the CLSM measurements.

This is possible if the emergent light beam after the second quarter-wave plate, 8 is split into an S-polarized beam, 18 and a P-polarized beam, 19 with a broadband polarizing beam splitter, 17. The dark- and bright-field, $I_{dark}$ and $I_{bright}$, images can be captured by two multi-channel CCD cameras 10 and 20 as shown in FIG. 14. Once k is found, $I_{dark}$(Birefringence) and $I_{bright}$(Birefringence) can be obtained from Eq. (21) and can be used to determine the wall thickness and fibril angle of the fibre. FIG. 15 shows the CPLM data after the k corrections versus the CLSM data. The slopes for the dark- and bright-field data are now 0.77 and 0.78, which is closer compared to data before corrections. The improvement for fibre wall thickness measurements is shown to be small, and unnecessary. However, the corrections are still needed for fibril angle measurements as they depend more on the absolute intensities.

The present invention provides a novel and unique method that can determine wall thickness and fibril angle rapidly and accurately in either wet or dry wood fibres non-destructively and non-invasively. The method requires the same minimal sample preparation as in fibre length measurements. Compared to other polarized light methods, the equation derived according to the present method is very simple even with the effects of the $S_1$ and $S_3$ layers included, which are critically important for the accuracy of the measurements. The relatively simple equation in this method is novel and unexpected, and makes the analysis of data for the determination of wall thickness and fibril angle of a fibre simple, rapid and reliable. Another important and unique feature of the present method is its robustness; the fibre wall thickness measurements are not affected significantly by the absorption and light scattering, as the measurements depend largely on the relative multi-wavelength intensities. Such robustness cannot be achieved with other methods. Unlike other methods described in Ye et al. [15, 16, 18] and Ye [P2, 17], the present method does not involve orienting the sample at a particular direction or making many measurements at various optical arrangements that involve physical movements. The measurements are independent of the orientations of the fibres in the optical system, and are performed under one optical arrangement. All necessary measurements can be obtained simultaneously and rapidly. The method does not require high precision optics or precise focusing for wall thickness and fibril angle measurements, since intensity measurements do not require high resolution as shown by the above experimental data. These advantages are particularly important for implementing this new method for measuring fibres in flow-through systems. This new invention has potential to measure wall thickness and fibril angle of individual wood fibres as fast as their fibre length measurements. Many of the existing commercial length analyzers use polarized light optics, but only for generating visual contrast for imaging purposes. This invention shows that with a set of well-matched precision achromatic quarter-wave retarders coupled with a proper multi-wavelength light source and imaging optics, and a multi-channel digital camera for detecting multi-wavelength intensities, these transmitted light intensities can be used not only for imaging purposes, but more importantly, for determining wall thickness and fibril angle of wood fibres according to the novel solutions provided in this invention.

REFERENCES CITED

Foreign Patent Documents
P1 WO 99/15877 April 1999 PCT Int'l Appl.
P2 WO 96/10168 April 1996 PCT Int'l Appl U.S. Patent Documents
P3 U.S. Pat. No. 5,311,290 May 1994 Olson et al. 356/383

Other Publications
1. Fengel, D. and Wegener, G., *Wood: Chemistry, ultrastructure, reactions,* Walter de Gruyter, Berlin (1984).
2. Seth, R. S., Jang, H. F., Chan, B. K., and Wu, C. B., "Transverse dimensions of wood pulp fibres and their implication for end use", in The Fundamentals of Papermaking Materials: Transactions of the Eleventh Fundamental Research Symposium held at Cambridge: September 1997, edited by C. F. Baker, PIRA International, Leatherhead, UK, pp. 473-503 (1997).
3. Paavilainen, L. "Importance of cross-dimensional fibre properties and coarseness for the characterization of softwood sulphate pulp", Paperi ja Puu 75(5): 343 (1993).
4. Harris, J. M. and Meylan, B. A., "The Influence of Microfibril Angle on Longitudinal and Tangential Shrinkage in *Pinus Radiata*", Holzforschung 19(5):144-153 (1965).
5. Page, D. H. and El-Hosseiny, F., "The Mechanical Properties of Single Wood Pulp Fibres. Part VI. Fibril Angle and the Shape of the Stress-Strain Curve", J. Pulp Paper Sci. 9(4): TR99-TR100 (1983).
6. Uesaka, T. and Moss, C., "Effects of Fibre Morphology on Hygroexpansivity of Paper: a Micromechanics Approach", Trans. Eleventh Fundamental Research Symposium held at Cambridge, September 1997, PIRA International, Leatherhead, Surrey, UK, pp. 663-679 (1997).
7. Richardson, J. D., Riddell, M. J. C. and Burrell, P., "Experience with the FibreLab™ V3.0 analyser for measuring fibre cross-section dimensions", Proceedings of the $57^{th}$ Appita Annual Conference: 315-322(2003).
8. Reme, P. A. and Helle, T., "Assessment of Transverse Dimensions of Wood Tracheids using SEM and Image Analysis", Holz als Roh- und Werkstoff 60:277-282 (2002).
9. Jang, H. F., Robertson, A. G., and Seth, R. S., "Transverse Dimensions of Wood Pulp Fibres by Confocal Laser Scanning Microscopy and Image Analysis", J. Mater. Sci. 27: 6391-6400 (1992).
10. Page, D. H., "A Method for Determining the Fibrillar Angle in Wood Tracheids", J. Microscopy Soc. 90(2): 137-143 (1969)
11. Huang, C. L., "Revealing Fibril Angle in Wood Sections by Ultrasonic Treatment", Wood and Fibre Sci. 27(1):49-54 (1995).
12. Pleasants, S., Batchelor, W. and Parker, I. H., "Measuring the Fibril Angle of Bleached Fibres Using Micro-Raman Spectroscopy", Proceedings of the $51^{st}$ Appita Annual General Conference (2):545-549 (1997).
13. Jang, H. F., "measurement of Fibril Angle in Wood Fibres with Polarization Confocal Microscopy", J. Pulp Paper Sci. 24(7): 224-230 (1998).
14. El-Hosseiny, F. and Page, D. H., "The Measurement of Fibril Angle of Wood Fibers Using Polarized Light", Wood and Fibre 5(3):208-214 (1973).
15. Ye, C., Sundström, M. O. and Remes, K., "Microscopic Transmission Ellipsometry: Measurement of the Fibril Angle and the Relative Phase Retardation of Single, Intact Wood Pulp Fibres", Applied Optics 33(28):6626-6637 (1994).
16. Ye, C. and Sundström, M. O., "Determination of $S_2$-Fibril-Angle and Fibril-Wall Thickness by Microscopic Transmission Ellipsometry", Tappi 80(6):181-190 (1997).
17. Ye, C., "Photopolarimetric Measurement of Single, Intact Pulp Fibres by Mueller Matrix Imaging Polarometry, Appl. Opt. 38(10): 1975-1985 (1999).
18. Ye, C. and Räty, J., "Estimation of Lignin Content in Single, Intact Pulp Fibres by UV Photometry and VIS Muller Matrix Polarimetry", Nordic Pulp and Paper Research J. 16(2): 143-148 (2001).

19. Page, D. H. and El-Hosseiny, F., "The Birefringence of Wood Pulp Fibres and the Thickness of the $S_1$ and $S_3$ Layers", Wood Fibre 6(3): 186-192 (1974).
20. Azzam, R. M. A. and Bashara, N. M., *Ellipsometry and Polarized Light*, North-Holland, New York, 1977.
21. Theocaria, P. S. and Gdoutos, E. E., *Matrix Theory of Photoelasticity*, Springer-Verlag, New York, 1979.
22. Gröbe A., Properties of Cellulose Materials, in *Polymer Handbook*, ed. by Brandrup, J., and Immergut, E. H., John Wiley & Sons, New York, Third Edition.
23. Siau, J. F., *Transport Processes in Wood*, Springer-Verlag, Berlin (1984)

The invention claimed is:

1. A method for determining relative phase retardations and orientations of the optical axes of different layer in a multi-layered birefringent cellulosic fibre specimen comprising the steps of:
   producing a circularly polarized light beam having a plurality of well-defined wavelengths, wherein the plurality is at least the same number as the number of parameters to be determined in the multi-layered specimen under evaluation;
   disposing said multi-layered birefringent cellulosic fibre specimen in said circuhrly polarized light beani in a non-restricted orientation;
   impinging the circularly polarized light beam on the multi-layered birefringent cellulosic fibre specimen;
   recording and measuring the light intensities of the plurality of well-defined wavelengths emergent from a circular analyzer located after the specimen;
   determining the relative phase retardations and orientations of the optical axes of different layers of the specimen from the light intensities of the emergent wavelengths by fitting the data with an equation that describes the specimen; and
   assessing the cellulosic fibre for use in a cellulosic fibre product based on the determination of the relative phase retardations and orientations of the optical axes of different layers of the specimen.

2. A method according to claim 1, wherein the circularly polarized light beam is in a dark field.

3. A method according to claim 1, wherein the circularly polarized light beam is in a bright field.

4. A method according to claim 1, wherein said multi-layered birefringent cellulosic fibre specimen is selected from cellulosic fibres consisting of wood and non-wood fibres, and wood and non-wood pulp fibres.

5. A method for determining, for pulp and paper manufacture, the relative phase retardation, related to wall thickness, and fibril angle of an intact wood fibre having a wall comprised of three layers $S_1$, $S_2$ and $S_3$: the two outside layers $S_1$ and $S_3$ having microfibrils oriented transversely with respect to the fibre longitudinal axis, and the middle dominant layer $S_2$ having microfibrils wound in a helix at fibril angle comprising the steps of:
   producing a circular polarized light system beam, at at least two wavelengths;
   impinging the circular polarized light beam on a wood fibre to be measured;
   recording and measuring the light intensities of the wavelengths emergent from a circular analyzer located after the wood fibre;
   determining the relative phase retardations in different layers and hence the wall thickness, and the $S_2$ fibril angle of the wood fibre from the light intensities of the wavelengths emergent from the wood fibre by fitting the data with an equation that describes the wood fibre; and
   assessing the wood fibre for pulp and rarer manufacture based on the determination of the relative phase retardations and orientations of the optical axes of different layers of the specimen.

6. A method according to claim 5, wherein the circularly polarized light beam is in a dark field.

7. A method according to claim 5, wherein the circularly polarized light beam is in a bright field.

8. An apparatus for determining relative phase retardations and orientations of the optical axes of different layers in a multi-layered birefringent cellulosic fibre specimen comprising a light source effective to provide light with multiple well-defined wavelengths,
   a circularly polarized light system to generate a circularly polarized light beam in a dark field and/or a bright field from the light from said light source,
   means to dispose a specimen within said system, in the path of the generated circularly polarized light beam,
   means for determining the light intensifies of individual well-defined wavelengths emergent from the circularly polarized light system, and
   processing and data analysis means to determine the properties of the specimen from the emergent light intensities, wherein the circularly polarized light system is comprised of a linear polarizer and a linear analyzer, and a pair of well-matched achromatic quarter-wave retarders therebetween, with a working wavelength range covering the wavelengths of the light source, with their optical axes oriented 90° to each other and 45° to the polarizer and the analyzer.

9. An apparatus according to claim 8, wherein said means for determining light intensities comprises:
   a condenser and an objective lens for microscopic polarized light imaging;
   an image capturer for capturing multiple circularly polarized light images of the specimen at the emergent wavelengths simultaneously;
   an image processing and analysis system, comprising an image processor for multiple channeled images to determine the light intensities at individual wavelengths, and an image analyzer for analyzing multiple images and for deciding the region of interest for data analysis.

10. An apparatus according to claim 9, wherein said image capturer is a multi-wavelength detector, multi-wavelength camera or multi-channel digital camera.

11. An apparatus according to claim 8, wherein said multi-layered birefringent specimen is selected from cellulosic fibres consisting of wood and non-wood fibres, and wood and non-wood pulp fibres.

12. An apparatus according to claim 8, wherein said light source provides a number of multiple well-defined predetermined wavelengths that are well separated, but are still within the acceptable working wavelength range of the achromatic quarter-wave retarders, the said wavelengths ranging from 250 nm to 1000 nm.

13. An apparatus for determining relative phase retardations and orientations of the optical axes of different layers in a multi-layered birefringent cellulosic fibre specimen comprising a light source effective to provide light with multiple well-defined wavelengths,
   a circularly polarized light system to generate a circularly polarized light beam in a dark field and/or a bright field from the light from said light source,
   means to dispose a specimen within said system, in the path of the generated circularly polarized light beam, means for determining the light intensities of individual well-defined wavelengths emergent from the circularly polarized light system, and processing and data analysis means to determine the properties of the specimen from the emergent light intensities, wherein said processing and data analysis means comprises;

a non-linear fitting routine for determining relative phase retardations and the orientations of the optical axes of a specimen, from data of intensities of the emergent wavelengths, from the circularly polarized light system.

14. An apparatus according to claim 13, wherein said multi-layered birefringent specimen is selected from cellulosic fibres consisting of wood and non-wood fibres, and wood and non-wood pulp fibres.

15. An apparatus according to claim 13, wherein said light source provides a number of multiple well-defined predetermined wavelengths that are well separated, but are still within the acceptable working wavelength range of the achromatic quarter-wave retarders, the said wavelengths ranging from 250 nm to 1000 nm.

* * * * *